United States Patent
Mandler et al.

(10) Patent No.: US 8,613,931 B2
(45) Date of Patent: *Dec. 24, 2013

(54) COMPOUNDS FOR TREATING BETA-AMYLOIDOSES

(75) Inventors: Markus Mandler, Vienna (AT); Christian Gieffers, Dossenheim (DE); Frank Mattner, Vienna (AT); Andrea Dolischka, Vienna (AT); Oleksandr Otava, Vienna (AT)

(73) Assignee: Affiris AG, Vienna (AT)

(*) Notice: Subject to any disclaimer, the term of this patent is extended or adjusted under 35 U.S.C. 154(b) by 53 days.

This patent is subject to a terminal disclaimer.

(21) Appl. No.: 12/997,674

(22) PCT Filed: Jun. 12, 2009

(86) PCT No.: PCT/AT2009/000236
§ 371 (c)(1),
(2), (4) Date: Dec. 13, 2010

(87) PCT Pub. No.: WO2009/149486
PCT Pub. Date: Dec. 17, 2009

(65) Prior Publication Data
US 2011/0097351 A1    Apr. 28, 2011

(30) Foreign Application Priority Data
Jun. 12, 2008 (AT) .................................. A 951/2008

(51) Int. Cl.
*A61K 39/00*    (2006.01)
*A61K 38/08*    (2006.01)
*C07K 7/06*    (2006.01)

(52) U.S. Cl.
USPC ........ 424/185.1; 530/326; 530/327; 530/328; 530/329

(58) Field of Classification Search
None
See application file for complete search history.

(56) References Cited

U.S. PATENT DOCUMENTS

| | | | |
|---|---|---|---|
| 2004/0123343 A1* | 6/2004 | La Rosa et al. | 800/278 |
| 2004/0265849 A1 | 12/2004 | Cargill et al. | |
| 2005/0176030 A1 | 8/2005 | Gan et al. | |
| 2006/0111301 A1 | 5/2006 | Mattner | |
| 2009/0004210 A1 | 1/2009 | Mattner et al. | |

FOREIGN PATENT DOCUMENTS

| | | |
|---|---|---|
| WO | WO 00/72880 A2 | 12/2000 |
| WO | WO 2004/062556 A2 | 7/2004 |
| WO | WO 2005023985 A2 * | 3/2005 |
| WO | WO 2006/005707 A2 | 1/2006 |
| WO | WO 2006/035237 A2 | 4/2006 |
| WO | WO 2006/045037 A2 | 4/2006 |
| WO | WO 2006/055178 A2 | 5/2006 |
| WO | WO 2008/002893 A2 | 1/2008 |
| WO | WO 2009091518 A2 * | 7/2009 |

OTHER PUBLICATIONS

Janus et al. (2000) Nature, 408:979-982.*
Krishnamurthy et al. (2011) New Biotechnol. 28(5):511-517.*
Kwan et al. (2005) Proc. Natl. Acad. Sci. USA, 102(14):5174-5179.*
Machida M et al. (2005) Nature, 438:1157-1161.*
Morgan et al. (2000) Nature, 408:982-985.*
Schenk et al. (1999) Nature, 400:173-177.*
Solomon (2002) Expert Opin. Biol. Ther. 2(8):907-917.*
Tuskan et al. (2006) Science, 313:1596-1604.*
Vickers JC (2002) Drugs Aging. 19(7):487-494.*
Xu et al. (2007) Proc. Natl. Acad. Sci. USA, 104(47):18730-18735.*
Petra Burgstaller, et al., "Aptamers and aptazymes: Accelerating small molecule drug discovery", Current Opinion in Drug Discovery & Development, vol. 5, No. 5, 2002, pp. 690-700.
Bart De Strooper, et al., "Proteolytic processing and cell biological functions of the amyloid precursor protein", Journal of Cell Science, 2000, pp. 1857-1870.
Michael Famulok, et al., "Nucleic Acid Aptamers—From Selection in Vitro to Applications in Vivo", Accounts of Chemical Research, vol. 33, No. 9, 2000, pp. 591-599.
Derek T. O'Hagan, et al., "Recent Advances in the Discovery and Delivery of Vaccine Adjuvants", Nature Reviews / Drug Discovery, vol. 2, Sep. 2003, pp. 727-735.
Jason T. Huse, et al., "β-Secretase Processing in the Trans-Golgi Network Preferentially Generates Truncated Amyloid Species That Accumulate in Alzheimer's Disease Brain", The Journal of Biological Chemistry, vol. 277, No. 18, May 3, 2002, pp. 16278-16284.
Günter Mayer, et al., "Controlling small guanine-nucleotide-exchange factor function through cytoplasmic RNA intramers", Proceedings of the National Academy of Sciences (PNAS), vol. 98, No. 9, Apr. 24, 2001, pp. 4961-4965.
William G.T. Willats, "Phage display: practicalities and prospects", Plant Molecular Biology, 2002, pp. 837-854.
Manmohan Singh, et al., "Advances in vaccine adjuvants", Nature Biotechnology, vol. 17, Nov. 1999, pp. 1075-1081.
International Search Report issued Apr. 8, 2010 in Application No. PCT/AT2009/000236.
Office Action issued Apr. 1, 2009 in Austria Application No. 4A A 951/2008—2 (English Translation).

(Continued)

*Primary Examiner* — Kimberly A Ballard
(74) *Attorney, Agent, or Firm* — Oblon, Spivak, McClelland, Maier & Neustadt, L.L.P.

(57) ABSTRACT

The present invention relates to the use of mimotopes in the treatment of diseases associated with β-amyloid formation and/or aggregation (β-Amyloidoses) including Alzheimer's disease, whereby said mimotopes are able to induce the in vivo formation of antibodies directed to Aβ1-40/42, AβpE3-40/42, Aβ3-40/42 and Aβ11-40/42.

15 Claims, 18 Drawing Sheets

(56) References Cited

OTHER PUBLICATIONS

Alex E. Roher, et al., "Amyloid beta peptides in human plasma and tissues and their significance for Alzheimer's disease", Alzheimer's and Dementia, vol. 5, No. 1, XP002572893, Jan. 1, 2009, pp. 18-29.

Markus Mandler, et al., "The MimoVax vaccine: A novel Alzheimer's treatment strategy targeting truncated Asz40/42 by active immunization", Alzheimer's and Dementia, vol. 5, No. 4, XP026253365, Jul. 1, 2009, p. 114.

Achim Schneeberger, et al., "Development of Alzheimer AFFITOPE vaccines—from concept to clinical testing", Alzheimer's and Dementia, vol. 5, No. 4, XP026220250, Jul. 1, 2009, p. 257.

J-M M, "Vaccine anti-Alzheimer" Revue Fracophone des Laboratoires, XP022667610, Jan. 1, 2008, p. 14.

Affiris Ag, "Alzheimer Impfung", Internet Citation, URL www.affiris.com/html/de/impfstoffe/morbus_alzheimer_interessierte_impfung.html, XP002572894, Mar. 9, 2010, 1 page.

M. Mandler et al.—Additional Experimental Data (2013).

* cited by examiner

```
                       SEQUENCE LISTING

<160> NUMBER OF SEQ ID NOS: 283

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 1

Ile Arg Trp Asp Thr Pro Cys
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 2

Val Arg Trp Asp Val Tyr Pro Cys
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 3

Ile Arg Tyr Asp Ala Pro Leu Cys
1               5

<210> SEQ ID NO 4
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 4

Ile Arg Tyr Asp Met Ala Gly Cys
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 5

Ile Arg Trp Asp Thr Ser Leu Cys
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 6

Ile Arg Trp Asp Gln Pro Cys
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 7

Ile Arg Trp Asp Gly Cys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 8

Ile Arg Trp Asp Gly Gly Cys
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 9

Glu Val Trp His Arg His Gln Cys
1               5
```

```
<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 10

Glu Arg Trp His Glu Lys His Cys
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 11

Glu Val Trp His Arg Leu Gln Cys
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 12

Glu Leu Trp His Arg Tyr Pro Cys
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 13

Glu Leu Trp His Arg Ala Phe Cys
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 14

Glu Leu Trp His Arg Ala Cys
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide
```

```
<400> SEQUENCE: 15

Glu Val Trp His Arg Gly Cys
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 16

Glu Val Trp His Arg His Cys
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 17

Glu Arg Trp His Glu Lys Cys
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 18

Gln Asp Phe Arg His Tyr Cys
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 19

Ser Glu Phe Lys His Gly Cys
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 20

Thr Ser Phe Arg His Gly Cys
1               5

<210> SEQ ID NO 21
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      mimotope peptide

<400> SEQUENCE: 21

Thr Ser Val Phe Arg His Cys
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 22

Thr Pro Phe Arg His Thr Cys
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 23

Ser Gln Phe Arg His Tyr Cys
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 24

Leu Met Phe Arg His Asn Cys
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 25

Ser Ala Phe Arg His His Cys
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 26

Leu Pro Phe Arg His Gly Cys
1               5
```

```
<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 27

Ser His Phe Arg His Gly Cys
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 28

Ile Leu Phe Arg His Gly Cys
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 29

Gln Phe Lys His Asp Leu Cys
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 30

Asn Trp Phe Pro His Pro Cys
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 31

Glu Glu Phe Lys Tyr Ser Cys
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 32
```

```
Asn Glu Leu Arg His Ser Thr Cys
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 33

Gly Glu Met Arg His Gln Pro Cys
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 34

Asp Thr Tyr Phe Pro Arg Ser Cys
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 35

Val Glu Leu Arg His Ser Arg Cys
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 36

Tyr Ser Met Arg His Asp Ala Cys
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 37

Ala Ala Asn Tyr Phe Pro Arg Cys
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                            mimotope peptide

<400> SEQUENCE: 38

Ser Pro Asn Gln Phe Arg His Cys
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 39

Ser Ser Ser Phe Phe Pro Arg Cys
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 40

Glu Asp Trp Phe Phe Trp His Cys
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 41

Ser Ala Gly Ser Phe Arg His Cys
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 42

Gln Val Met Arg His His Ala Cys
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 43

Ser Glu Phe Ser His Ser Ser Cys
1               5

<210> SEQ ID NO 44
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 44

Gln Pro Asn Leu Phe Tyr His Cys
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 45

Glu Leu Phe Lys His His Leu Cys
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 46

Thr Leu His Glu Phe Arg His Cys
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 47

Ala Thr Phe Arg His Ser Pro Cys
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 48

Ala Pro Met Tyr Phe Pro His Cys
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 49

Thr Tyr Phe Ser His Ser Leu Cys
1               5
```

```
<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 50

His Glu Pro Leu Phe Ser His Cys
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 51

Ser Leu Met Arg His Ser Ser Cys
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 52

Glu Phe Leu Arg His Thr Leu Cys
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 53

Ala Thr Pro Leu Phe Arg His Cys
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 54

Gln Glu Leu Lys Arg Tyr Tyr Cys
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide
```

-continued

```
<400> SEQUENCE: 55

Thr His Thr Asp Phe Arg His Cys
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 56

Leu His Ile Pro Phe Arg His Cys
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 57

Asn Glu Leu Phe Lys His Phe Cys
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 58

Ser Gln Tyr Phe Pro Arg Pro Cys
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 59

Asp Glu His Pro Phe Arg His Cys
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 60

Met Leu Pro Phe Arg His Gly Cys
1               5

<210> SEQ ID NO 61
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      mimotope peptide

<400> SEQUENCE: 61

Ser Ala Met Arg His Ser Leu Cys
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 62

Thr Pro Leu Met Phe Trp His Cys
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 63

Leu Gln Phe Lys His Ser Thr Cys
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 64

Ala Thr Phe Arg His Ser Thr Cys
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 65

Thr Gly Leu Met Phe Lys His Cys
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 66

Ala Glu Phe Ser His Trp His Cys
1               5
```

```
<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 67

Gln Ser Glu Phe Lys His Trp Cys
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 68

Ala Glu Phe Met His Ser Val Cys
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 69

Ala Asp His Asp Phe Arg His Cys
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 70

Asp Gly Leu Leu Phe Lys His Cys
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 71

Ile Gly Phe Arg His Asp Ser Cys
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 72
```

```
Ser Asn Ser Glu Phe Arg Arg Cys
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 73

Ser Glu Leu Arg His Ser Thr Cys
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 74

Thr His Met Glu Phe Arg Arg Cys
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 75

Glu Glu Leu Arg His Ser Val Cys
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 76

Gln Leu Phe Lys His Ser Pro Cys
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 77

Tyr Glu Phe Arg His Ala Gln Cys
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
```

-continued mimotope peptide

<400> SEQUENCE: 78

Ser Asn Phe Arg His Ser Val Cys
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 79

Ala Pro Ile Gln Phe Arg His Cys
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 80

Ala Tyr Phe Pro His Thr Ser Cys
1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 81

Asn Ser Ser Glu Leu Arg His Cys
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 82

Thr Glu Phe Arg His Lys Ala Cys
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 83

Thr Ser Thr Glu Met Trp His Cys
1               5

<210> SEQ ID NO 84
<211> LENGTH: 8

```
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 84

Ser Gln Ser Tyr Phe Lys His Cys
1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 85

Cys Ser Glu Phe Lys His
1               5

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 86

Ser Glu Phe Lys His Cys
1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 87

Cys His Glu Phe Arg His
1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 88

His Glu Phe Arg His Cys
1               5

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 89

Asp Ala Glu Phe Arg His Asp Ser Gly Tyr Cys
1               5                   10
```

```
<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 90

Glu Phe Arg His Asp Ser Cys
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 91

Glu Val His His Gln Lys Cys
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: pyroGlu

<400> SEQUENCE: 92

Glu Phe Arg His Asp Ser Cys
1               5

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: pyroGlu

<400> SEQUENCE: 93

Glu Val His His Gln Lys Leu Val Phe Cys
1               5                   10

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 94

Gly Tyr Glu Val His His Gln Lys Cys
1               5
```

```
<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 95

Glu Val His His Gln Lys Leu Val Phe Cys
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 96

Cys Glu Val His His Gln Lys Leu Val Phe Phe
1               5                   10

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 97

Cys Gly Leu Met Val Gly Gly Val Val
1               5

<210> SEQ ID NO 98
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 99
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

```
<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (3)..(3)
<223> OTHER INFORMATION: Trp or Tyr
<220> FEATURE:
<221> NAME/KEY: MOD_RES
<222> LOCATION: (5)..(5)
<223> OTHER INFORMATION: Thr, Val, Ala, Met, Gln or Gly
<220> FEATURE:
<221> NAME/KEY: MOD_RES
<222> LOCATION: (6)..(6)
<223> OTHER INFORMATION: Pro, Ala, Tyr, Ser, Cys, Gly or absent
<220> FEATURE:
<221> NAME/KEY: MOD_RES
<222> LOCATION: (7)..(7)
<223> OTHER INFORMATION: Pro, Leu, Gly, Cys or absent
<220> FEATURE:
<221> NAME/KEY: MOD_RES
<222> LOCATION: (8)..(8)
<223> OTHER INFORMATION: May or may not be present

<400> SEQUENCE: 100

Xaa Arg Xaa Asp Xaa Xaa Xaa Cys
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (2)..(2)
<223> OTHER INFORMATION: Val, Arg or Leu
<220> FEATURE:
<221> NAME/KEY: MOD_RES
<222> LOCATION: (5)..(5)
<223> OTHER INFORMATION: Arg or Glu
<220> FEATURE:
<221> NAME/KEY: MOD_RES
<222> LOCATION: (6)..(6)
<223> OTHER INFORMATION: Ala, His, Lys, Leu, Tyr or Gly
<220> FEATURE:
<221> NAME/KEY: MOD_RES
<222> LOCATION: (7)..(7)
<223> OTHER INFORMATION: Pro, His, Phe, Gln, Cys or absent
<220> FEATURE:
<221> NAME/KEY: MOD_RES
<222> LOCATION: (8)..(8)
<223> OTHER INFORMATION: May or may not be present

<400> SEQUENCE: 101

Glu Xaa Trp His Xaa Xaa Xaa Cys
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
``` amyloid-beta fragment peptide

<400> SEQUENCE: 102

Glu Phe Arg His Asp Ser Gly Tyr
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      amyloid-beta fragment peptide
<220> FEATURE:
<221> NAME/KEY: MOD_RES
<222> LOCATION: (1)..(1)
<223> OTHER INFORMATION: pyroGlu

<400> SEQUENCE: 103

Glu Phe Arg His Asp Ser Gly Tyr
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      amyloid-beta fragment peptide

<400> SEQUENCE: 104

Glu Val His His Gln Lys Leu
1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      amyloid-beta fragment peptide

<400> SEQUENCE: 105

Asp Ala Glu Phe Arg
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 106

Ile Arg Trp Asp Thr Pro Cys
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (8)..(8)
<223> OTHER INFORMATION: May or may not be present

<400> SEQUENCE: 107

Val Arg Trp Asp Val Tyr Pro Cys
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 108

Ile Arg Tyr Asp Ala Pro Leu Cys
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 109

Ile Arg Tyr Asp Met Ala Gly Cys
1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 110

Ile Arg Trp Asp Thr Ser Leu Cys
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 111

Ile Arg Trp Asp Gln Pro Cys
1               5
```

```
<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: May or may not be present

<400> SEQUENCE: 112

Ile Arg Trp Asp Gly Cys
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 113

Ile Arg Trp Asp Gly Gly Cys
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 114

Glu Val Trp His Arg His Gln Cys
1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 115

Glu Arg Trp His Glu Lys His Cys
1               5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (8)..(8)
<223> OTHER INFORMATION: May or may not be present

<400> SEQUENCE: 116

Glu Val Trp His Arg Leu Gln Cys
1               5

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 117

Glu Leu Trp His Arg Tyr Pro Cys
1               5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 118

Glu Leu Trp His Arg Ala Phe Cys
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 119

Glu Leu Trp His Arg Ala Cys
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 120
```

```
Glu Val Trp His Arg Gly Cys
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 121

Glu Val Trp His Arg His Cys
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 122

Glu Arg Trp His Glu Lys Cys
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 123

Gln Asp Phe Arg His Tyr Cys
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 124

Ser Glu Phe Lys His Gly Cys
1               5

<210> SEQ ID NO 125
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 125

Thr Ser Phe Arg His Gly Cys
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 126

Thr Ser Val Phe Arg His Cys
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 127

Thr Pro Phe Arg His Thr Cys
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 128

Ser Gln Phe Arg His Tyr Cys
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present
```

```
<400> SEQUENCE: 129

Leu Met Phe Arg His Asn Cys
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 130

Ser Ala Phe Arg His His Cys
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 131

Leu Pro Phe Arg His Gly Cys
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 132

Ser His Phe Arg His Gly Cys
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 133

Ile Leu Phe Arg His Gly Cys
1               5

<210> SEQ ID NO 134
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 134

Gln Phe Lys His Asp Leu Cys
1               5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 135

Asn Trp Phe Pro His Pro Cys
1               5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 136

Glu Glu Phe Lys Tyr Ser Cys
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 137

Asn Glu Leu Arg His Ser Thr Cys
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
```

```
<223> OTHER INFORMATION: May or may not be present

<400> SEQUENCE: 138

Gly Glu Met Arg His Gln Pro Cys
1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 139

Asp Thr Tyr Phe Pro Arg Ser Cys
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 140

Val Glu Leu Arg His Ser Arg Cys
1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 141

Tyr Ser Met Arg His Asp Ala Cys
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 142

Ala Ala Asn Tyr Phe Pro Arg Cys
1               5
```

```
<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 143

Ser Pro Asn Gln Phe Arg His Cys
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 144

Ser Ser Ser Phe Phe Pro Arg Cys
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 145

Glu Asp Trp Phe Phe Trp His Cys
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 146

Ser Ala Gly Ser Phe Arg His Cys
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (8)..(8)
<223> OTHER INFORMATION: May or may not be present

<400> SEQUENCE: 147

Gln Val Met Arg His His Ala Cys
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 148

Ser Glu Phe Ser His Ser Ser Cys
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 149

Gln Pro Asn Leu Phe Tyr His Cys
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 150

Glu Leu Phe Lys His His Leu Cys
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 151

Thr Leu His Glu Phe Arg His Cys
1               5
```

```
<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 152

Ala Thr Phe Arg His Ser Pro Cys
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 153

Ala Pro Met Tyr Phe Pro His Cys
1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 154

Thr Tyr Phe Ser His Ser Leu Cys
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 155

His Glu Pro Leu Phe Ser His Cys
1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (8)..(8)
<223> OTHER INFORMATION: May or may not be present

<400> SEQUENCE: 156

Ser Leu Met Arg His Ser Ser Cys
1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 157

Glu Phe Leu Arg His Thr Leu Cys
1               5

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 158

Ala Thr Pro Leu Phe Arg His Cys
1               5

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 159

Gln Glu Leu Lys Arg Tyr Tyr Cys
1               5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 160
```

```
Thr His Thr Asp Phe Arg His Cys
1               5
```

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 161

```
Leu His Ile Pro Phe Arg His Cys
1               5
```

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 162

```
Asn Glu Leu Phe Lys His Phe Cys
1               5
```

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 163

```
Ser Gln Tyr Phe Pro Arg Pro Cys
1               5
```

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 164

```
Asp Glu His Pro Phe Arg His Cys
1               5
```

<210> SEQ ID NO 165
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 165

Met Leu Pro Phe Arg His Gly Cys
1               5

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 166

Ser Ala Met Arg His Ser Leu Cys
1               5

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 167

Thr Pro Leu Met Phe Trp His Cys
1               5

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 168

Leu Gln Phe Lys His Ser Thr Cys
1               5

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present
```

```
<400> SEQUENCE: 169

Ala Thr Phe Arg His Ser Thr Cys
1               5

<210> SEQ ID NO 170
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 170

Thr Gly Leu Met Phe Lys His Cys
1               5

<210> SEQ ID NO 171
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 171

Ala Glu Phe Ser His Trp His Cys
1               5

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 172

Gln Ser Glu Phe Lys His Trp Cys
1               5

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 173

Ala Glu Phe Met His Ser Val Cys
1               5

<210> SEQ ID NO 174
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 174

Ala Asp His Asp Phe Arg His Cys
1               5

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 175

Asp Gly Leu Leu Phe Lys His Cys
1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 176

Ile Gly Phe Arg His Asp Ser Cys
1               5

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 177

Ser Asn Ser Glu Phe Arg Arg Cys
1               5

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
```

```
<223> OTHER INFORMATION: May or may not be present

<400> SEQUENCE: 178

Ser Glu Leu Arg His Ser Thr Cys
1               5

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 179

Thr His Met Glu Phe Arg Arg Cys
1               5

<210> SEQ ID NO 180
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 180

Glu Glu Leu Arg His Ser Val Cys
1               5

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 181

Gln Leu Phe Lys His Ser Pro Cys
1               5

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 182

Tyr Glu Phe Arg His Ala Gln Cys
1               5
```

```
<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 183

Ser Asn Phe Arg His Ser Val Cys
1               5

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 184

Ala Pro Ile Gln Phe Arg His Cys
1               5

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 185

Ala Tyr Phe Pro His Thr Ser Cys
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 186

Asn Ser Ser Glu Leu Arg His Cys
1               5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (8)..(8)
<223> OTHER INFORMATION: May or may not be present

<400> SEQUENCE: 187

Thr Glu Phe Arg His Lys Ala Cys
1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 188

Thr Ser Thr Glu Met Trp His Cys
1               5

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 189

Ser Gln Ser Tyr Phe Lys His Cys
1               5

<210> SEQ ID NO 190
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 190

Cys Ser Glu Phe Lys His
1               5

<210> SEQ ID NO 191
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: May or may not be present

<400> SEQUENCE: 191

Ser Glu Phe Lys His Cys
1               5
```

```
<210> SEQ ID NO 192
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 192

Cys His Glu Phe Arg His
1               5

<210> SEQ ID NO 193
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: May or may not be present

<400> SEQUENCE: 193

His Glu Phe Arg His Cys
1               5

<210> SEQ ID NO 194
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 194

His His His His His His
1               5

<210> SEQ ID NO 195
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ile Arg Trp Asp Thr Pro
1               5

<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Val Arg Trp Asp Val Tyr Pro
1               5
```

```
<210> SEQ ID NO 197
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ile Arg Tyr Asp Ala Pro Leu
1               5

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ile Arg Tyr Asp Met Ala Gly
1               5

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ile Arg Trp Asp Thr Ser Leu
1               5

<210> SEQ ID NO 200
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ile Arg Trp Asp Gln Pro
1               5

<210> SEQ ID NO 201
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ile Arg Trp Asp Gly
1               5

<210> SEQ ID NO 202
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202
```

```
Ile Arg Trp Asp Gly Gly
1               5

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Glu Val Trp His Arg His Gln
1               5

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Glu Arg Trp His Glu Lys His
1               5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Glu Val Trp His Arg Leu Gln
1               5

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Glu Leu Trp His Arg Tyr Pro
1               5

<210> SEQ ID NO 207
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Glu Leu Trp His Arg Ala Phe
1               5

<210> SEQ ID NO 208
<211> LENGTH: 6
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 208

Glu Leu Trp His Arg Ala
1               5

<210> SEQ ID NO 209
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Glu Val Trp His Arg Gly
1               5

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Glu Val Trp His Arg His
1               5

<210> SEQ ID NO 211
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Glu Arg Trp His Glu Lys
1               5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gln Asp Phe Arg His Tyr
1               5

<210> SEQ ID NO 213
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ser Glu Phe Lys His Gly
1               5

<210> SEQ ID NO 214
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Thr Ser Phe Arg His Gly
1               5

<210> SEQ ID NO 215
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Thr Ser Val Phe Arg His
1               5

<210> SEQ ID NO 216
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Thr Pro Phe Arg His Thr
1               5

<210> SEQ ID NO 217
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ser Gln Phe Arg His Tyr
1               5

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Leu Met Phe Arg His Asn
1               5

<210> SEQ ID NO 219
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ser Ala Phe Arg His His
1               5
```

```
<210> SEQ ID NO 220
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Leu Pro Phe Arg His Gly
1               5

<210> SEQ ID NO 221
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ser His Phe Arg His Gly
1               5

<210> SEQ ID NO 222
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ile Leu Phe Arg His Gly
1               5

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gln Phe Lys His Asp Leu
1               5

<210> SEQ ID NO 224
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Asn Trp Phe Pro His Pro
1               5

<210> SEQ ID NO 225
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 225

Glu Glu Phe Lys Tyr Ser
1               5

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Asn Glu Leu Arg His Ser Thr
1               5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Glu Met Arg His Gln Pro
1               5

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Asp Thr Tyr Phe Pro Arg Ser
1               5

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Val Glu Leu Arg His Ser Arg
1               5

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Tyr Ser Met Arg His Asp Ala
1               5

<210> SEQ ID NO 231
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 231

Ala Ala Asn Tyr Phe Pro Arg
1               5

<210> SEQ ID NO 232
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ser Pro Asn Gln Phe Arg His
1               5

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ser Ser Ser Phe Phe Pro Arg
1               5

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Glu Asp Trp Phe Phe Trp His
1               5

<210> SEQ ID NO 235
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Ala Gly Ser Phe Arg His
1               5

<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gln Val Met Arg His His Ala
1               5
```

```
<210> SEQ ID NO 237
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ser Glu Phe Ser His Ser Ser
1               5

<210> SEQ ID NO 238
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gln Pro Asn Leu Phe Tyr His
1               5

<210> SEQ ID NO 239
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Glu Leu Phe Lys His His Leu
1               5

<210> SEQ ID NO 240
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Thr Leu His Glu Phe Arg His
1               5

<210> SEQ ID NO 241
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ala Thr Phe Arg His Ser Pro
1               5

<210> SEQ ID NO 242
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242
```

```
Ala Pro Met Tyr Phe Pro His
1               5

<210> SEQ ID NO 243
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Thr Tyr Phe Ser His Ser Leu
1               5

<210> SEQ ID NO 244
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

His Glu Pro Leu Phe Ser His
1               5

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ser Leu Met Arg His Ser Ser
1               5

<210> SEQ ID NO 246
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Glu Phe Leu Arg His Thr Leu
1               5

<210> SEQ ID NO 247
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Ala Thr Pro Leu Phe Arg His
1               5

<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 248

Gln Glu Leu Lys Arg Tyr Tyr
1               5

<210> SEQ ID NO 249
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Thr His Thr Asp Phe Arg His
1               5

<210> SEQ ID NO 250
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Leu His Ile Pro Phe Arg His
1               5

<210> SEQ ID NO 251
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Asn Glu Leu Phe Lys His Phe
1               5

<210> SEQ ID NO 252
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ser Gln Tyr Phe Pro Arg Pro
1               5

<210> SEQ ID NO 253
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Asp Glu His Pro Phe Arg His
1               5

<210> SEQ ID NO 254
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Met Leu Pro Phe Arg His Gly
1               5

<210> SEQ ID NO 255
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ser Ala Met Arg His Ser Leu
1               5

<210> SEQ ID NO 256
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Thr Pro Leu Met Phe Trp His
1               5

<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Leu Gln Phe Lys His Ser Thr
1               5

<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ala Thr Phe Arg His Ser Thr
1               5

<210> SEQ ID NO 259
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Thr Gly Leu Met Phe Lys His
1               5
```

```
<210> SEQ ID NO 260
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Ala Glu Phe Ser His Trp His
1               5

<210> SEQ ID NO 261
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gln Ser Glu Phe Lys His Trp
1               5

<210> SEQ ID NO 262
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ala Glu Phe Met His Ser Val
1               5

<210> SEQ ID NO 263
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ala Asp His Asp Phe Arg His
1               5

<210> SEQ ID NO 264
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Asp Gly Leu Leu Phe Lys His
1               5

<210> SEQ ID NO 265
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 265

Ile Gly Phe Arg His Asp Ser
1               5

<210> SEQ ID NO 266
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ser Asn Ser Glu Phe Arg Arg
1               5

<210> SEQ ID NO 267
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ser Glu Leu Arg His Ser Thr
1               5

<210> SEQ ID NO 268
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Thr His Met Glu Phe Arg Arg
1               5

<210> SEQ ID NO 269
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Glu Glu Leu Arg His Ser Val
1               5

<210> SEQ ID NO 270
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gln Leu Phe Lys His Ser Pro
1               5

<210> SEQ ID NO 271
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 271

Tyr Glu Phe Arg His Ala Gln
1               5

<210> SEQ ID NO 272
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ser Asn Phe Arg His Ser Val
1               5

<210> SEQ ID NO 273
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ala Pro Ile Gln Phe Arg His
1               5

<210> SEQ ID NO 274
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Ala Tyr Phe Pro His Thr Ser
1               5

<210> SEQ ID NO 275
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Asn Ser Ser Glu Leu Arg His
1               5

<210> SEQ ID NO 276
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Thr Glu Phe Arg His Lys Ala
1               5
```

```
<210> SEQ ID NO 277
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Thr Ser Thr Glu Met Trp His
1               5

<210> SEQ ID NO 278
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ser Gln Ser Tyr Phe Lys His
1               5

<210> SEQ ID NO 279
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Ser Glu Phe Lys His
1               5

<210> SEQ ID NO 280
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

His Glu Phe Arg His
1               5

<210> SEQ ID NO 281
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Glu Phe Arg His Asp Ser
1               5

<210> SEQ ID NO 282
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

<223> OTHER INFORMATION: pyroGlu

<400> SEQUENCE: 282

Glu Phe Arg His Asp Ser
1               5

<210> SEQ ID NO 283
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Glu Val His His Gln Lys
1               5

COMPOUNDS FOR TREATING BETA-AMYLOIDOSES

The present invention relates to the use of mimotopes for the prevention, treatment and diagnosis of diseases associated with α-amyloid formation and/or aggregation (β-Amyloidoses).

Various degenerative diseases are characterized by the aberrant polymerization and accumulation of specific proteins. These so called proteopathies include neurological disorders such as Alzheimer's disease, Parkinson's disease and Huntington's disease as well as diverse systemic disorders including the amyloidoses. The present invention relates to the prevention, treatment and diagnosis of proteopathies associated with β-amyloid proteins summarised under the term β-Amyloidoses. The most prominent form of β-Amyloidoses is Alzheimer's disease (AD). Other examples include but are not limited to Dementia with Lewy bodies and Dementia in Down syndrome.

AD is characterized by the abnormal accumulation of extracellular amyloid plaques—closely associated with extensive astrocytosis and microgliosis as well as dystrophic neurones and neuronal loss. These amyloid plaques mainly consist of the Amyloid-β (Aβ) peptides Aβ40 and Aβ42 derived from the Amyloid Precursor Protein (APP), which is expressed on various cell types in the nervous system. Aβ peptides are considered to be directly involved in the pathogenesis and progression of AD.

APP is normally processed by two cleavage steps to form the currently known forms of Abeta x-40/42/43. The first cleavage is performed by the so called beta-site APP-cleaving enzymes 1 and 2 (BACE1 and BACE2); the second proteolytic step is performed by the gamma-Secretase Complex (reviewed in De Strooper et al. J Cell Sci 113 (2000): 1857-1870).

BACE enzymes recognise two sites in the N-terminal portion of the presumptive Aβ peptide: the first interaction of BACE with APP leads to a cut at the sequence DAEFR (SEQ ID NO: 105) (pos. 1 in Aβ) and formation of Abeta 1-X. Alternatively BACE can also cut at future position 11 within Aβ resulting in the fragment 11-X. Thus BACE mediated APP processing creates a variety of different Aβ species with full length Abeta 1-40/42 as major contribuent. Gamma-Secretase activity leads to production of 3 main fragments: Aβ 1-40/42/43. Once these peptides are produced they are further processed by Amino-peptidases resulting in their subsequent stepwise degradation. These further steps lead to formation of other forms like for example Aβ3-40/42 respectively. In humans on average 60-85% of amyloid plaque material is formed by Aβ40/42 derivatives which are N-terminally truncated and frequently modified. The relative amounts of N-terminally truncated Aβ species are variable in respect of Aβlevels, mutations and BACE activity.

The most abundant truncated forms of Aβ are: Aβ3-40/42 and Aβ1'-40/42. Both peptides contain an N-terminal glutamate residue, which is frequently modified enzymatically to pyroglutamate, resulting in the formation of Aβ3 (pE)-40/42 and Aβ11(pE)-40/42, respectively. Because the amino terminus of the Abeta 3(pE) and 11(pE) peptides is blocked by internal lactam, it is protected from the proteolytic action of aminopeptidases other than pyroglutamate-specific ones and can thus remain stable in tissues.

The most prominent form of N-terminally truncated modified amyloid is formed by the peptide 3(pE)-40/42, which is thought to constitute up to 50% of all truncated forms. This means that this isoforms constitute 25-40% of all amyloid peptides in AD brains. Another prominent form of truncated Aβ peptides is Aβ11-40/42: Naslund et al. and Huse et al. could demonstrate that there is a significant level of these truncated species detectable in human brains of AD patients as well as in infra-clinical patients for AD. Furthermore these peptides undergo intramolecular dehydration and form stable (pE) forms with similar consequences as described for 3(pE)-40/42.

It has been shown previously that truncated and modified peptides are more stable in neural tissue than full length Aβ. Additionally, N-terminally truncated forms of Aβ are more amyloidogenic than unmodified Aβ peptides, thus enhancing the rate of plaque formation, and also show neurotoxic activity when applied to neurons in culture as well as in in vivo experiments. Truncated forms of Aβ can already be detected in diffuse aggregations of Aβ in early stages of AD and might be involved in early plaque formation, acting as individual seeds in vivo.

There is compelling evidence that the occurrence of N-terminally truncated Aβ species is correlated with increasing severity and early onset of neurodegeneration in sporadic and familial Alzheimer disease as well as Down Syndrome patients. The aggregatory effects in conjunction with the increased stability of these peptides make them a potentially dangerous player in AD development. Analysis in infraclinical patients suffering from familial AD or Down-Syndrome have unequivocally shown that Aβ 3 (pE)-42 can be detected during the earliest stages of disease, also called the "seed" stages. At this time no or only minor neurological symptoms can be detected although plaques are starting to accumulate which bear the Aβ 3 (pE)-42 peptide species. Thus, data from such patients are implying a link between early formation of truncated Aβ species and disease onset as well as progression.

In light of these findings it seems to be important to decrease the amount of these peptide species in AD patients to modify disease progression and reduce toxicity and accompanying cognitive decline. An optimal AD-vaccine should thus elicit an immune response which is able to target the most prominent forms of Aβ peptides present in the brain of AD patients.

Indeed, immunotherapeutic treatment using active and passive immunisation strategies to target full length Aβ, led to reduction of Aβ plaques and had beneficial impact on disease progression in animal models of AD. Passive vaccination experiments in mouse models of AD clearly showed, that antibodies specifically directed against the N- and C-termini of Aβ40/42 are able to reduce plaque burden in the brain and also improve cognitive functions in treated animals as judged from behavioural analyses. Similar observations have been made in active vaccination experiments, using different approaches to induce immune responses directed against Aβ40/42 in mice. All of these approaches used full length Aβ40/42 or fragments containing the native sequence of Aβ and most reduced the amyloid burden in transgenic mouse models. Importantly, these animals also showed improved cognitive functions. Strikingly, Lernere et al. (Am J Pathol 165 (2004): 283-297) could reproduce these results in non-human primates which showed clear reduction of plaque deposition and associated pathology in response to active vaccination with full length Aβ. However, the first phase IIa clinical vaccination trial in AD patients using full length Aβ42 as antigen had to be discontinued due to severe neuroinflammatory side effects including brain infiltration of autoreactive T-cells. Nevertheless, studies investigating the clinical effects in patients treated with AN-1792 revealed that patients who developed an antibody response against Aβ42 but did not suffer from meningoen-cephalitis performed better in cognitive tests than non-responding patients, indicating that immunotherapy might be a very useful treatment approach in AD.

Most importantly, recent results obtained from autopsy cases analysing patients which underwent AN1792 vaccination showed a clearance of full length Aβ species from the brain but a persistence of N-terminally truncated forms of Aβ. This underscores the necessity of the invention of novel vaccines which are targeting full length Aβ as well as N-terminally truncated and modified forms of this molecule.

Inducing an immune response against Aβ40/42 peptides in humans can interfere with cognitive decline in AD patients, but a safe Alzheimer vaccine has to avoid the formation of autoreactive T cells. Vaccination using native Aβ40/42 peptides or fragments thereof suffers from the intrinsic risk of inducing autoimmune disease in patients, as the immune response cannot exclusively be targeted to Aβ.

It is an object of the present invention to provide compounds and medicaments which can be used to treat and/or prevent β-Amyloidoses including Alzheimer's disease. These compounds should show no or a significantly reduced risk of inducing autoimmune diseases when administered to an individual. According to another object of the present invention said compound may be able to induce the in vivo formation of antibodies in an individual which are directed to truncated and/or stabilised forms of Aβ, which usually are the major components of amyloid deposits.

Therefore the present invention relates to the use of at least one compound comprising the amino acid sequence

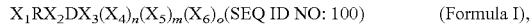

X$_1$RX$_2$DX$_3$(X$_4$)$_n$(X$_5$)$_m$(X$_6$)$_o$(SEQ ID NO: 100)  (Formula I), wherein
X$_1$ is isoleucine (I) or valine (V),
X$_2$ is tryptophan (W) or tyrosine (Y),
X$_3$ is threonine (T), valine (V), alanine (A), methionine (M), glutamine (Q) or glycine (G),
X$_4$ is proline (P), alanine (A), tyrosine (Y), serine (S), cysteine (C) or glycine (G),
X$_5$ is proline (P), leucine (L), glycine (G) or cysteine (C),
X$_6$ is cysteine (C),
n, m and o are, independently, 0 or 1,
said compound having a binding capacity to an antibody which is specific for an epitope of the amyloid-beta-peptide (Aβ) comprising the amino acid sequence EFRHDSGY (SEQ ID NO: 102) and/or pEFRHDSGY (SEQ ID NO: 103) for producing a medicament for preventing and/or treating β-amyloidoses.

It surprisingly turned out, that a compound comprising an amino acid sequence of the formula I is able to induce the in vivo formation of antibodies which are directed to the truncated Aβ forms AβpE3-40/42 and Aβ3-40/42. The antibodies formed are able to bind to said Aβ fragments resulting in the disintegration of Aβ plaques.

Formula I and II and all other peptidic molecules disclosed herein mimic the natural occurring Aβ peptides and variants Aβ1-40/42, AβpE3-40/42, Aβ3-40/42 and Aβ11-40/42, so that compounds comprising the amino acid sequences disclosed herein are able to induce the formation of respective antibodies.

The invention presented herein refers to antigens which do not contain sequences of the native Aβ peptide and mimic the structure of neo-epitopes not detectable by mimotopes such as described in WO 2004/062556. Such a mimotope-based AD vaccine would therefore induce antibody responses exclusively reacting with the pathological Aβ molecules mentioned herein but not with parental structures like APP. Furthermore, mimotopes do not contain potential T-cell self-epitopes and avoid induction of detrimental autoreactive T-cells.

"β-Amyloidoses", as used herein, refers to various degenerative diseases which are characterized by the aberrant polymerization and accumulation of specific proteins so called proteopathies. The present invention relates to the prevention, treatment and diagnosis of proteopathies associated with β-amyloid proteins summarized under the term β-Amyloidoses. The most prominent form of β-Amyloidoses is Alzheimer's disease (AD). Other examples include but are not limited to Dementia with Lewy bodies and Dementia in Down syndrome. Further examples are Lewy body dementia, myositis, sporadic inclusion body myositis, hereditary cerebral hemorrhage with amyloidosis (dutch type), cerebral amyloid angiopathy, Aβ related angiitis.

According to a particularly preferred embodiment of the present invention "β-Amyloidoses" is Alzheimer's disease.

According to a preferred embodiment of the present invention the compound comprises a peptide having an amino acid sequence selected from the group consisting of IRWDTP(C) (SEQ ID NO: 106), VRWDVYP(C) (SEQ ID NO: 107), IRYDAPL(C) (SEQ ID NO: 108), IRYDMAG(C) (SEQ ID NO: 109), IRWDTSL(C) (SEQ ID NO: 110), IRWDQP(C) (SEQ ID NO: 111), IRWDG(C) (SEQ ID NO: 112) and IRWDGG(C) (SEQ ID NO: 113).

Particularly preferred compounds of the present invention comprise or consist of the above identified amino acid sequences, whereby the C-terminus of said peptide may or may not comprise a cysteine residue (indicated by the use of brackets) so that the compound obtained may be coupled, e.g., to a carrier molecule. However, it is of course also possible to link to the N-terminus of said peptide a cysteine residue.

According to a particularly preferred embodiment of the present invention the amino acid sequence is IRWDTP(C) (SEQ ID NO: 106), VRWDVYP(C) (SEQ ID NO: 107), IRYDAPL(C) (SEQ ID NO: 108) or IRYDMAG(C) (SEQ ID NO: 109).

Another aspect of the present invention relates to the use of at least one compound comprising the amino acid sequence

EX$_1$WHX$_2$X$_3$(X$_4$)$_n$(X$_5$)$_m$(SEQ ID NO: 101)  (Formula II), wherein
X$_1$ is valine (V), arginine (R) or leucine (L),
X$_2$ is arginine (R) or glutamic acid (E),
X$_3$ is alanine (A), histidine (H), lysine (K), leucine (L), tyrosine (Y) or glycine (G),
X$_4$ is proline (P), histidine (H), phenylalanine (F), glutamine (Q) or cysteine (C)
X$_5$ is cysteine (C),
n and m are, independently, 0 or 1,
said compound having a binding capacity to an antibody which is specific for an epitope of the amyloid-beta-peptide (Aβ) comprising the amino acid sequence EVHHQKL (SEQ ID NO: 104) for producing a medicament for preventing and/or treating β-amyloidoses.

The administration of a compound comprising an amino acid sequence of formula II provokes an immune response against the truncated Aβ form Aβ11-40/42.

According to a preferred embodiment of the present invention the compound comprises a peptide having an amino acid sequence selected from the group consisting of EVWHRHQ (C) (SEQ ID NO: 114), ERWHEKH(C) (SEQ ID NO: 115), EVWHRLQ(C) (SEQ ID NO: 116), ELWHRYP(C) (SEQ ID NO: 117), ELWHRAF(C) (SEQ ID NO: 118), ELWHRA(C)

(SEQ ID NO: 119), EVWHRG(C) (SEQ ID NO: 120), EVWHRH(C) (SEQ ID NO: 121) and ERWHEK(C) (SEQ ID NO: 122), preferably EVWHRHQ(C) (SEQ ID NO: 114), ERWHEKH(C) (SEQ ID NO: 115), EVWHRLQ(C) (SEQ ID NO: 116), ELWHRYP(C) (SEQ ID NO: 117) and ELWHRAF(C) (SEQ ID NO: 118).

Another aspect of the present invention relates to the use of at least one compound comprising an amino acid sequence selected from the group consisting of QDFRHY(C) (SEQ ID NO: 123), SEFKHG(C) (SEQ ID NO: 124), TSFRHG(C) (SEQ ID NO: 125), TSVFRH(C) (SEQ ID NO: 126), TPFRHT(C) (SEQ ID NO: 127), SQFRHY(C) (SEQ ID NO: 128), LMFRHN(C) (SEQ ID NO: 129), SAFRHH(C) (SEQ ID NO: 130), LPFRHG(C) (SEQ ID NO: 131), SHFRHG(C) (SEQ ID NO: 132), ILFRHG(C) (SEQ ID NO: 133), QFKHDL(C) (SEQ ID NO: 134), NWFPHP(C) (SEQ ID NO: 135), EEFKYS(C) (SEQ ID NO: 136), NELRHST(C) (SEQ ID NO: 137), GEMRHQP(C) (SEQ ID NO: 138), DTYFPRS(C) (SEQ ID NO: 139), VELRHSR(C) (SEQ ID NO: 140), YSMRHDA(C) (SEQ ID NO: 141), AANYFPR(C) (SEQ ID NO: 142), SPNQFRH(C) (SEQ ID NO: 143), SSSFFPR(C) (SEQ ID NO: 144), EDWFFWH(C) (SEQ ID NO: 145), SAGSFRH(C) (SEQ ID NO: 146), QVMRHHA(C) (SEQ ID NO: 147), SEFSHSS(C) (SEQ ID NO: 148), QPNLFYH(C) (SEQ ID NO: 149), ELFKHHL(C) (SEQ ID NO: 150), TLHEFRH(C) (SEQ ID NO: 151), ATFRHSP(C) (SEQ ID NO: 152), APMYFPH(C) (SEQ ID NO: 153), TYFSHSL(C) (SEQ ID NO: 154), HEPLFSH(C) (SEQ ID NO: 155), SLMRHSS(C) (SEQ ID NO: 156), EFLRHTL(C) (SEQ ID NO: 157), ATPLFRH(C) (SEQ ID NO: 158), QELKRYY(C) (SEQ ID NO: 159), THTDFRH(C) (SEQ ID NO: 160), LHIPFRH(C) (SEQ ID NO: 161), NELFKHF(C) (SEQ ID NO: 162), SQYFPRP(C) (SEQ ID NO: 163), DEHPFRH(C) (SEQ ID NO: 164), MLPFRHG(C) (SEQ ID NO: 165), SAMRHSL(C) (SEQ ID NO: 166), TPLMFWH(C) (SEQ ID NO: 167), LQFKHST(C) (SEQ ID NO: 168), ATFRHST(C) (SEQ ID NO: 169), TGLMFKH(C) (SEQ ID NO: 170), AEFSHWH(C) (SEQ ID NO: 171), QSEFKHW(C) (SEQ ID NO: 172), AEFMHSV(C) (SEQ ID NO: 173), ADHDFRH(C) (SEQ ID NO: 174), DGLLFKH(C) (SEQ ID NO: 175), IGFRHDS(C) (SEQ ID NO: 176), SNSEFRR(C) (SEQ ID NO: 177), SELRHST(C) (SEQ ID NO: 178), THMEFRR(C) (SEQ ID NO: 179), EELRHSV(C) (SEQ ID NO: 180), QLFKHSP(C) (SEQ ID NO: 181), YEFRHAQ(C) (SEQ ID NO: 182), SNFRHSV(C) (SEQ ID NO: 183), APIQFRH(C) (SEQ ID NO: 184), AYFPHTS(C) (SEQ ID NO: 185), NSSELRH(C) (SEQ ID NO: 186), TEFRHKA(C) (SEQ ID NO: 187), TSTEMWH(C) (SEQ ID NO: 188), SQSYFKH(C) (SEQ ID NO: 189), (C)SEFKH (SEQ ID NO: 190), SEFKH(C) (SEQ ID NO: 191), (C)HEFRH (SEQ ID NO: 192) and HEFRH(C) (SEQ ID NO: 193) for producing a medicament for preventing and/or treating (β-amyloidoses.

Each of these compounds is able to induce the in vivo formation of antibodies directed to Aβ1-40/42, AβpE3-40/42 and Aβ3-40/42. Therefore these compounds are particularly well suited to treat and/or prevent β-amyloidoses, such as AD, because the administration of one compound results in the formation of anti-bodies which are capable to recognize the three major Aβ forms Aβ1-40/42, AβpE3-40/42 and Aβ3-40/42.

According to a preferred embodiment of the present invention the compound comprises or consists of a peptide having an amino acid sequence selected from the group consisting of QDFRHY(C) (SEQ ID NO: 123), SEFKHG(C) (SEQ ID NO: 124), TSFRHG(C) (SEQ ID NO: 125), TSVFRH(C) (SEQ ID NO: 126), TPFRHT(C) (SEQ ID NO: 127), SQFRHY(C) (SEQ ID NO: 128), LMFRHN(C) (SEQ ID NO: 129), SAFRHH(C) (SEQ ID NO: 130), LPFRHG(C) (SEQ ID NO: 131), SHFRHG(C) (SEQ ID NO: 132), ILFRHG(C) (SEQ ID NO: 133), QFKHDL(C) (SEQ ID NO: 134), NWFPHP(C) (SEQ ID NO: 135), EEFKYS(C) (SEQ ID NO: 136), SPNQFRH(C) (SEQ ID NO: 143), TLHEFRH(C) (SEQ ID NO: 151), THTDFRH(C) (SEQ ID NO: 160), DEHPFRH(C) (SEQ ID NO: 164), QSEFKHW(C) (SEQ ID NO: 172), ADHDFRH(C) (SEQ ID NO: 174), DGLLFKH(C) (SEQ ID NO: 175), EELRHSV(C) (SEQ ID NO: 180), TEFRHKA(C) (SEQ ID NO: 187), (C)SEFKH (SEQ ID NO: 190), SEFKH(C) (SEQ ID NO: 191), (C)HEFRH (SEQ ID NO: 192) and HEFRH(C) (SEQ ID NO: 193) preferably SEFKHG(C) (SEQ ID NO: 124), TSVFRH(C) (SEQ ID NO: 126), SQFRHY(C) (SEQ ID NO: 128), LMFRHN(C) (SEQ ID NO: 129), ILFRHG(C) (SEQ ID NO: 133), SPNQFRH(C) (SEQ ID NO: 143), ELFKHHL(C) (SEQ ID NO: 150), TLHEFRH(C) (SEQ ID NO: 151), THTDFRH(C) (SEQ ID NO: 160), DEHPFRH(C) (SEQ ID NO: 164), QSEFKHW(C) (SEQ ID NO: 172), ADHDFRH(C) (SEQ ID NO: 174), YEFRHAQ(C) (SEQ ID NO: 182), TEFRHKA(C) (SEQ ID NO: 187).

The amino acid sequences disclosed herein are considered to be mimotopes of the epitopes of Aβ comprising the amino acid sequence EFRHDSGY (SEQ ID NO: 102), pEFRHDSGY (SEQ ID NO: 103) or EVHHQKL (SEQ ID NO: 104). According to the present invention the term "mimotope" refers to a molecule which has a conformation that has a topology equivalent to the epitope of which it is a mimic. The mimotope binds to the same antigen-binding region of an antibody which binds immunospecifically to a desired antigen. The mimotope will elicit an immunological response in a host that is reactive to the antigen to which it is a mimic. The mimotope may also act as a competitor for the epitope of which it is a mimic in in vitro inhibition assays (e.g. ELISA inhibition assays) which involve the epitope and an antibody binding to said epitope. However, a mimotope of the present invention may not necessarily prevent or compete with the binding of the epitope of which it is a mimic in an in vitro inhibition assay although it is capable to induce a specific immune response when administered to a mammal.

As used herein, the term "epitope" refers to an immunogenic region of an antigen which is recognized by a particular anti-body molecule. In general, an antigen will possess one or more epitopes, each capable of binding an antibody that recognizes the particular epitope.

The mimotopes of the present invention can be synthetically produced by chemical synthesis methods which are well known in the art, either as an isolated peptide or as a part of another peptide or polypeptide. Alternatively, the peptide mimotope can be produced in a microorganism which produces the peptide mimotope which is then isolated and if desired, further purified. The peptide mimotope can be produced in microorganisms such as bacteria, yeast or fungi, in eukaryote cells such as a mammalian or an insect cell, or in a recombinant virus vector such as adenovirus, poxvirus, herpesvirus, Simliki forest virus, baculovirus, bacteriophage, sindbis virus or sendai virus. Suitable bacteria for producing the peptide mimotope include *E. coli, B. subtilis* or any other bacterium that is capable of expressing peptides such as the peptide mimotope. Suitable yeast types for expressing the peptide mimotope include *Saccharomyces cerevisiae, Schizosaccharomyces pombe, Candida, Pichia pastoris* or any other yeast capable of expressing peptides. Corresponding methods are well known in the art. Also methods for isolating and purifying recombinantly produced peptides are well known in the art and include e.g. as gel filtration, affinity chromatography, ion exchange chromatography etc.

To facilitate isolation of the peptide mimotope, a fusion polypeptide may be made wherein the peptide mimotope is translationally fused (covalently linked) to a heterologous polypeptide which enables isolation by affinity chromatography. Typical heterologous polypeptides are His-Tag (e.g. His$_6$ (SEQ ID NO: 194); 6 histidine residues (SEQ ID NO: 194)), GST-Tag (Glutathione-Stransferase) etc. The fusion polypeptide facilitates not only the purification of the mimotopes but can also prevent the mimotope polypeptide from being degraded during purification. If it is desired to remove the heterologous polypeptide after purification the fusion polypeptide may comprise a cleavage site at the junction between the peptide mimotope and the heterologous polypeptide. The cleavage site consists of an amino acid sequence that is cleaved with an enzyme specific for the amino acid sequence at the site (e.g. proteases).

The mimotopes of the present invention may also be modified at or nearby their N- and/or C-termini so that at said positions a cysteine residue is bound thereto. In a preferred embodiment terminally positioned (located at the N- and C-termini of the peptide) cysteine residues are used to cyclize the peptides through a disulfide bond. The cysteine residue may also serve to bind to said peptide/compound a further molecule (e.g. a carrier).

The mimotopes of the present invention may also be used in various assays and kits, in particular in immunological assays and kits. Therefore, it is particularly preferred that the mimotope may be part of another peptide or polypeptide, particularly an enzyme which is used as a reporter in immunological assays. Such reporter enzymes include e.g. alkaline phosphatase or horseradish peroxidase.

The mimotopes according to the present invention preferably are antigenic polypeptides which in their amino acid sequence vary from the amino acid sequence of Aβ or of fragments of Aβ. In this respect, the inventive mimotopes may not only comprise amino acid substitutions of one or more naturally occurring amino acid residues but also of one or more non-natural amino acids (i.e. not from the 20 "classical" amino acids) or they may be completely assembled of such non-natural amino acids. Moreover, the inventive antigens which induce antibodies directed and binding to Aβ1-40/42, AβpE3-40/42, Aβ3-40/42 and Aβ11-40/42 may be assembled of D- or L-amino acids or of combinations of DL-amino acids and, optionally, they may have been changed by further modifications, ring closures or derivatizations. Suitable antibody-inducing antigens may be provided from commercially available peptide libraries. Preferably, these peptides are at least 7 amino acids, and preferred lengths may be up to 16, preferably up to 14 or 20 amino acids (e.g. 5 to 16 amino acid residues). According to the invention, however, also longer peptides may very well be employed as antibody-inducing antigens. Furthermore the mimotopes of the present invention may also be part of a polypeptide and consequently comprising at their N- and/or C-terminus at least one further amino acid residue.

For preparing the mimotopes of the present invention (i.e. the antibody-inducing antigens disclosed herein), of course also phage libraries, peptide libraries are suitable, for instance produced by means of combinatorial chemistry or obtained by means of high throughput screening techniques for the most varying structures (Display: A Laboratory Manual by Carlos F. Barbas (Editor), et al.; Willats W G Phage display: practicalities and prospects. Plant Mol. Biol. 2002 December; 50(6):837-54).

Furthermore, according to the invention also anti-Aβ1-40/42-, -AβpE3-40/42-, -Aβ3-40/42- and -Aβ11-40/42-antibody-inducing antigens based on nucleic acids ("aptamers") may be employed, and these, too, may be found with the most varying (oligonucleotide) libraries (e.g. with 2-180 nucleic acid residues) (e.g. Burgstaller et al., Curr. Opin. Drug Discov. Dev. 5(5) (2002), 690-700; Famulok et al., Acc. Chem. Res. 33 (2000), 591-599; Mayer et al., PNAS 98 (2001), 4961-4965, etc.). In antibody-inducing antigens based on nucleic acids, the nucleic acid backbone can be provided e.g. by the natural phosphor-diester compounds, or also by phosphorotioates or combinations or chemical variations (e.g. as PNA), wherein as bases, according to the invention primarily U, T, A, C, G, H and mC can be employed. The 2'-residues of the nucleotides which can be used according to the present invention preferably are H, OH, F, Cl, $NH_2$, O-methyl, O-ethyl, O-propyl or O-butyl, wherein the nucleic acids may also be differently modified, i.e. for instance with protective groups, as they are commonly employed in oligonucleotide synthesis. Thus, aptamer-based antibody-inducing antigens are also preferred antibody-inducing antigens within the scope of the present invention.

According to a preferred embodiment of the present invention the compound is coupled to a pharmaceutically acceptable carrier, preferably KLH (Keyhole Limpet Hemocyanin), tetanus toxoid, albumin-binding protein, bovine serum albumin, a dendrimer (MAP; Biol. Chem. 358: 581), peptide linkers (or flanking regions) as well as the adjuvant substances described in Singh et al., Nat. Biotech. 17 (1999), 1075-1081 (in particular those in Table 1 of that document), and O'Hagan et al., Nature Re-views, Drug Discovery 2 (9) (2003), 727-735 (in particular the endogenous immuno-potentiating compounds and delivery systems described therein), or mixtures thereof. The conjugation chemistry (e.g. via heterobifunctional compounds such as GMBS and of course also others as described in "Bioconjugate Techniques", Greg T. Hermanson) in this context can be selected from reactions known to the skilled man in the art. Moreover, the vaccine composition may be formulated with an adjuvant, preferably a low soluble aluminium composition, in particular aluminium hydroxyide. Of course, also adjuvants like MF59 aluminium phosphate, calcium phosphate, cytokines (e.g., IL-2, IL-12, GM-CSF), saponins (e.g., QS21), MDP derivatives, CpG oligos, LPS, MPL, polyphosphazenes, emulsions (e.g., Freund's, SAF), liposomes, virosomes, iscoms, cochleates, PLG microparticles, poloxamer particles, virus-like particles, heat-labile enterotoxin (LT), cholera toxin (CT), mutant toxins (e.g., LTK63 and LTR72), microparticles and/or polymerized liposomes may be used.

The compound of the present invention is preferably bound to the carrier or adjuvant via a linker, which is selected from the group consisting of NHS-poly (ethylene oxide) (PEO) (e.g. NHS-PEO$_4$-maleimide).

A vaccine which comprises the present compound (mimotope) and the pharmaceutically acceptable carrier may be administered by any suitable mode of application, e.g. i.d., i.v., i.p., i.m., intranasally, orally, subcutaneously, etc. and in any suitable delivery device (O'Hagan et al., Nature Reviews, Drug Discovery 2 (9), (2003), 727-735). The compound of the present invention is preferably formulated for intravenous, subcutaneous, intradermal or intramuscular administration (see e.g. "Handbook of Pharmaceutical Manufacturing Formulations", Sarfaraz Niazi, CRC Press Inc, 2004).

The medicament (vaccine) according to the present invention contains the compound according to the invention in an amount of from 0.1 ng to 10 mg, preferably 10 ng to 1 mg, in particular 100 ng to 100 μg, or, alternatively, e.g. 100 fmol to 10 μmol, preferably 10 μmol to 1 μmol, in particular 100 μmol to 100 nmol. Typically, the vaccine may also contain auxiliary substances, e.g. buffers, stabilizers etc.

Another aspect of the present invention relates to the use of a compound as defined above for treating and/or ameliorating symptoms of synucleopathy.

It surprisingly turned out that the compounds of the present invention can also be used to treat and ameliorate symptoms associated with synucleopathies.

Amyloidoses and synucleopathies are associated with the cerebral accumulation of β-amyloid and α-synuclein, respectively. Some patients show clinical and pathological features of both diseases, raising the possibility of overlapping pathogenic pathways. These patients are also classified as suffering from a newly identified syndrome described as Dementia with Lewy Bodies or Parkinson's disease with dementia (DLB/PDD). In a recent transgenic animal model for DLB/PDD it has been shown that overexpression of both, ☐synuclein and Amyloid Precursor Protein (hAPP), in mice leads to the development of cognitive and motor alterations accompanied by loss of cholinergic neurons and reduction in synaptic vesicles, formation of extensive amyloid plaques, and haSYN-immunoreactive intraneuronal fibrillar inclusions. All of these features are also found in the DLB/PDD syndrome. It has been described recently that both molecules are potentially able to interact and to form hybrid oligomers in vitro. It has also been shown that overexpression of the APP can exacerbate some of the pathologic effects of α-synuclein overexpression. In contrast, α-synuclein is able to enhance secretion and toxicity of amyloid beta peptides and could thus also increase the effects of β-amyloid supporting the notion of overlapping pathogenic pathways in neurodegenerative processes.

In both proteopathies progressive accumulation of peptide oligomers has been identified as one of the central toxic events leading to the various alterations typical for either synucleopathies or amyloidoses. Despite this mechanistic similarity, it is hypothesized that α-synuclein and Aβ have distinct, as well as convergent, pathogenic effects on the integrity and function of the brain. Synucleins are believed to affect motoric function ore severely than cognitive function, whereas amyloid β peptides are described to have opposite effects. The reason for this discrepancy is currently unknown but it precludes a clear description of the interdependencies and effects of both molecules.

The treatment approach presented in the current invention is describing an immunotherapy targeting Aβ which will lead to the removal of mainly extracellular amyloid. It is thus believed to relieve the amyloid associated alterations ranging from plaque deposition to neuronal death as well as to memory problems and cognitive decline. The subcellular localization of synucleins however indicates that these intracellular proteins are mainly active at the synapse, especially confined to synaptic vesicles. Interestingly, also synuclein accumulations, which are the unifying pathologic hallmark of synucleopathies, are mainly detectable intracellularly. Additionally, the pathogenic mechanism underlying synucleopathies is believed to be attributable to intraneuronal changes ranging from mitochondrial dysfunction, accumulation of abnormally folded, ubiquitinated or phosphorylated proteins as well as accumulation of alpha synuclein. These alterations are consequently resulting in changes in synaptic functions, synaptic failure, and loss of dopaminergic neurons and classical clinical signs of synucleopathies. In contrast Aβ is mainly detectable extraneuronally and amyloid plaques as well as fibrils, protofibrils and oligomers of beta amyloid can exert neurotoxic functions when applied extracellularly or intracerebrally. Thus it is a surprising finding to the expert that an approach mainly targeting extracellular amyloid would reduce the symptoms of synucleopathies like PD, which are affecting mainly intracellular processes leading to the typical symptoms described below. It is even more surprising as it is currently believed that the overlapping effects of both molecules are caused by direct interactions of the two proteins which should mainly occur intracellularly. According to the present invention the term "synucleinopathy" includes all neurodegenerative disorders characterized by pathological synuclein aggregations. Several neurodegenerative disorders including Parkinson's Disease (PD), Lewy Body Disease (LBD), Diffuse Lewy Body Disease (DLBD), Dementia with Lewy Bodies (DLB), Parkinsonism with Dementia (PDD), Multiple System Atrophy (MSA) and Neurodegeneration with Brain Iron Accumulation type I (NBIA Type I) are collectively grouped as synucleinopathies.

"Symptoms of synucleopathy", as used herein, refers to those symptoms of the synucleopathies, in particular Parkinson's disease, which affect the motor and non-motor behaviour of a patient suffering from said disease. "Motor symptoms" include resting tremor, Bradykinesia, rigidity, postural instability, stooped posture, dystonia, fatigue, impaired fine motor dexterity and motor coordination, impaired gross motor coordination, poverty of movement (decreased arm swing), akathisia, speech problems, such as softness of voice or slurred speech caused by lack of muscle control, loss of facial expression, or "masking", micrographia, difficulty swallowing, sexual dysfunction, drooling etc. "Non-motor" symptoms include pain, dementia or confusion, sleep disturbances, constipation, skin problems, depression, fear or anxiety, memory difficulties and slowed thinking, urinary problems, fatigue and aching, loss of energy, compulsive behaviour, cramping etc.

According to a preferred embodiment of the present invention the synucleopathy is selected from the group of Parkinson's Disease, Dementia with Lewy Bodies, multiple system atrophy and neurodegeneration with brain iron accumulation. Particularly preferred is Parkinson's disease.

Another aspect of the present invention relates to a peptide having or consisting of an amino acid sequence selected from the group consisting of IRWDTP(C) (SEQ ID NO: 106), VRWDVYP(C) (SEQ ID NO: 107), IRYDAPL(C) (SEQ ID NO: 108), IRYDMAG(C) (SEQ ID NO: 109), IRWDTSL(C) (SEQ ID NO: 110), IRWDQP(C) (SEQ ID NO: 111), IRWDG(C) (SEQ ID NO: 112), IRWDGG(C) (SEQ ID NO: 113), EVWHRHQ(C) (SEQ ID NO: 114), ERWHEKH(C) (SEQ ID NO: 115), EVWHRLQ(C) (SEQ ID NO: 116), ELWHRYP(C) (SEQ ID NO: 117), ELWHRAF(C) (SEQ ID NO: 118), ELWHRA(C) (SEQ ID NO: 119), EVWHRG(C) (SEQ ID NO: 120), EVWHRH(C) (SEQ ID NO: 121), ERWHEK(C) (SEQ ID NO: 122), QDFRHY(C) (SEQ ID NO: 123), SEFKHG(C) (SEQ ID NO: 124), TSFRHG(C) (SEQ ID NO: 125), TSVFRH(C) (SEQ ID NO: 126), TPFRHT(C) (SEQ ID NO: 127), SQFRHY(C) (SEQ ID NO: 128), LMFRHN(C) (SEQ ID NO: 129), SAFRHH(C) (SEQ ID NO: 130), LPFRHG(C) (SEQ ID NO: 131), SHFRHG(C) (SEQ ID NO: 132), ILFRHG(C) (SEQ ID NO: 133), QFKHDL(C) (SEQ ID NO: 134), NWFPHP(C) (SEQ ID NO: 135), EEFKYS(C) (SEQ ID NO: 136), NELRHST(C) (SEQ ID NO: 137), GEMRHQP(C) (SEQ ID NO: 138), DTYFPRS(C) (SEQ ID NO: 139), VELRHSR(C) (SEQ ID NO: 140), YSMRHDA(C) (SEQ ID NO: 141), AANYFPR(C) (SEQ ID NO: 142), SPNQFRH(C) (SEQ ID NO: 143), SSSFFPR(C) (SEQ ID NO: 144), EDWFFWH(C) (SEQ ID NO: 145), SAGSFRH(C) (SEQ ID NO: 146), QVMRHHA(C) (SEQ ID NO: 147), SEFSHSS(C) (SEQ ID NO: 148), QPNLFYH(C) (SEQ ID NO: 149), ELFKHHL(C) (SEQ ID NO: 150), TLHEFRH(C) (SEQ ID NO: 151), ATFRHSP(C) (SEQ ID NO: 152), APMYFPH(C) (SEQ ID NO: 153), TYFSHSL(C) (SEQ ID NO: 154), HEPLFSH(C) (SEQ ID NO: 155), SLMRHSS(C) (SEQ ID NO: 156), EFLRHTL(C) (SEQ ID NO: 157), ATPLFRH(C) (SEQ ID NO: 158), QELKRYY(C) (SEQ ID NO: 159), THTDFRH(C) (SEQ ID NO: 160), LHIPFRH(C) (SEQ ID NO: 161), NELFKHF(C) (SEQ ID NO: 162), SQYFPRP(C) (SEQ ID NO: 163), DEHPFRH(C) (SEQ ID NO: 164), MLPFRHG(C) (SEQ ID NO: 165), SAMRHSL(C) (SEQ ID NO: 166), TPLMFWH(C) (SEQ ID NO: 167), LQFKHST(C) (SEQ ID NO: 168), ATFRHST(C) (SEQ ID NO: 169), TGLMFKH(C) (SEQ ID NO: 170), AEFSHWH (C) (SEQ ID NO: 171), QSEFKHW(C) (SEQ ID NO: 172), AEFMHSV(C) (SEQ ID NO: 173), ADHDFRH(C) (SEQ ID NO: 174), DGLLFKH(C) (SEQ ID NO: 175), IGFRHDS(C) (SEQ ID NO: 176), SNSEFRR(C) (SEQ ID NO: 177), SELRHST(C) (SEQ ID NO: 178), THMEFRR(C) (SEQ ID NO: 179), EELRHSV(C) (SEQ ID NO: 180), QLFKHSP(C) (SEQ ID NO: 181), YEFRHAQ(C) (SEQ ID NO: 182), SNFRHSV(C) (SEQ ID NO: 183), APIQFRH(C) (SEQ ID NO: 184), AYFPHTS(C) (SEQ ID NO: 185), NSSELRH(C) (SEQ ID NO: 186), TEFRHKA(C) (SEQ ID NO: 187), TSTEMWH(C) (SEQ ID NO: 188), SQSYFKH(C) (SEQ ID NO: 189), (C)SEFKH (SEQ ID NO: 190), SEFKH(C) (SEQ ID NO: 191), (C)HEFRH (SEQ ID NO: 192) and HEFRH(C) (SEQ ID NO: 193). As indicated by the use of the parenthesis the peptides of the present invention may or may not comprise the cysteine residue at the C- or N-terminus. Consequently the present invention encompasses also the following amino acid sequences: IRWDTP (SEQ ID NO: 195), VRWDVYP (SEQ ID NO: 196), IRYDAPL (SEQ ID NO: 197), IRYDMAG (SEQ ID NO: 198), IRWDTSL (SEQ ID NO: 199), IRWDQP (SEQ ID NO: 200), IRWDG (SEQ ID NO: 201), IRWDGG (SEQ ID NO: 202), EVWHRHQ (SEQ ID NO: 203), ERWHEKH (SEQ ID NO: 204), EVWHRLQ (SEQ ID NO: 205), ELWHRYP (SEQ ID NO: 206), ELWHRAF (SEQ ID NO: 207), ELWHRA (SEQ ID NO: 208), EVWHRG (SEQ ID NO: 209), EVWHRH (SEQ ID NO: 210), ERWHEK (SEQ ID NO: 211), QDFRHY (SEQ ID NO: 212), SEFKHG (SEQ ID NO: 213), TSFRHG (SEQ ID NO: 214), TSVFRH (SEQ ID NO: 215), TPFRHT (SEQ ID NO: 216), SQFRHY (SEQ ID NO: 217), LMFRHN (SEQ ID NO: 218), SAFRHH (SEQ ID NO: 219), LPFRHG (SEQ ID NO: 220), SHFRHG (SEQ ID NO: 221), ILFRHG (SEQ ID NO: 222), QFKHDL (SEQ ID NO: 223), NWFPHP (SEQ ID NO: 224), EEFKYS (SEQ ID NO: 225), NELRHST (SEQ ID NO: 226), GEMRHQP (SEQ ID NO: 227), DTYFPRS (SEQ ID NO: 228), VELRHSR (SEQ ID NO: 229), YSMRHDA (SEQ ID NO: 230), AANYFPR (SEQ ID NO: 231), SPNQFRH (SEQ ID NO: 232), SSSFFPR (SEQ ID NO: 233), EDWFFWH (SEQ ID NO: 234), SAGSFRH (SEQ ID NO: 235), QVMRHHA (SEQ ID NO: 236), SEFSHSS (SEQ ID NO: 237), QPNLFYH (SEQ ID NO: 238), ELFKHHL (SEQ ID NO: 239), TLHEFRH (SEQ ID NO: 240), ATFRHSP (SEQ ID NO: 241), APMYFPH (SEQ ID NO: 242), TYFSHSL (SEQ ID NO: 243), HEPLFSH (SEQ ID NO: 244), SLMRHSS (SEQ ID NO: 245), EFLRHTL (SEQ ID NO: 246), ATPLFRH (SEQ ID NO: 247), QELKRYY (SEQ ID NO: 248), THTDFRH (SEQ ID NO: 249), LHIPFRH (SEQ ID NO: 250), NELFKHF (SEQ ID NO: 251), SQYFPRP (SEQ ID NO: 252), DEHPFRH (SEQ ID NO: 253), MLPFRHG (SEQ ID NO: 254), SAMRHSL (SEQ ID NO: 255), TPLMFWH (SEQ ID NO: 256), LQFKHST (SEQ ID NO: 257), ATFRHST (SEQ ID NO: 258), TGLMFKH (SEQ ID NO: 259), AEFSHWH (SEQ ID NO: 260), QSEFKHW (SEQ ID NO: 261), AEFMHSV (SEQ ID NO: 262), ADHDFRH (SEQ ID NO: 263), DGLLFKH (SEQ ID NO: 264), IGFRHDS (SEQ ID NO: 265), SNSEFRR (SEQ ID NO: 266), SELRHST (SEQ ID NO: 267), THMEFRR (SEQ ID NO: 268), EELRHSV (SEQ ID NO: 269), QLFKHSP (SEQ ID NO: 270), YEFRHAQ (SEQ ID NO: 271), SNFRHSV (SEQ ID NO: 272), APIQFRH (SEQ ID NO: 273), AYFPHTS (SEQ ID NO: 274), NSSELRH (SEQ ID NO: 275), TEFRHKA (SEQ ID NO: 276), TSTEMWH (SEQ ID NO: 277), SQSYFKH (SEQ ID NO: 278), (C)SEFKH (SEQ ID NO: 190), SEFKH (SEQ ID NO: 279), HEFRH (SEQ ID NO: 280) and HEFRH (SEQ ID NO: 280).

According to a preferred embodiment the peptide is coupled to a pharmaceutically acceptable carrier, preferably KLH (Keyhole Limpet Hemocyanin).

Yet another aspect of the present invention relates to a pharmaceutical formulation, preferably a vaccine, comprising at least one peptide according to the present invention. Said pharmaceutical formulation may be employed to treat individuals suffering from β-Amyloidoses including Alzheimer's disease or prevent the formation of Aβ-plaques in an individual to impede the formation of β-Amyloidoses including Alzheimer's disease.

The present invention is further illustrated by the following figures and examples, however without being restricted thereto.

Figure 9:
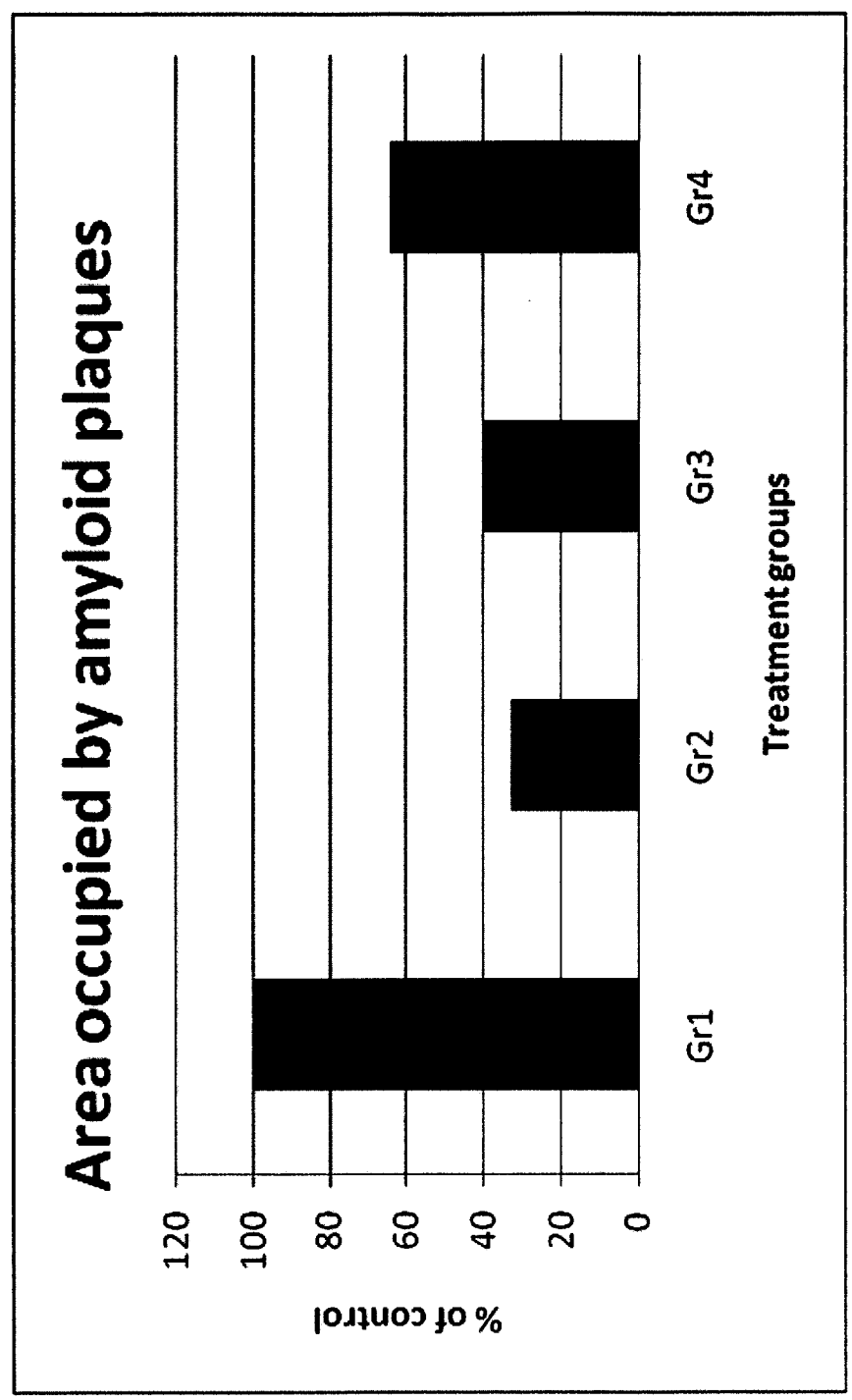

FIG. 9 shows areas occupied by amyloid plaques. Tg2576 were injected 6 times with mimotope vaccines adjuvanted with aluminium hydroxide (ALUM) by s.c. inoculation at monthly intervals. Control mice received PBS-ALUM only. Area occupied by amyloid plaques shown as percent of the control group. Gr1 . . . control group; Gr2 . . . received p4381; Gr3 . . . received p4390; Gr4 . . . received p4715

Figure 10:
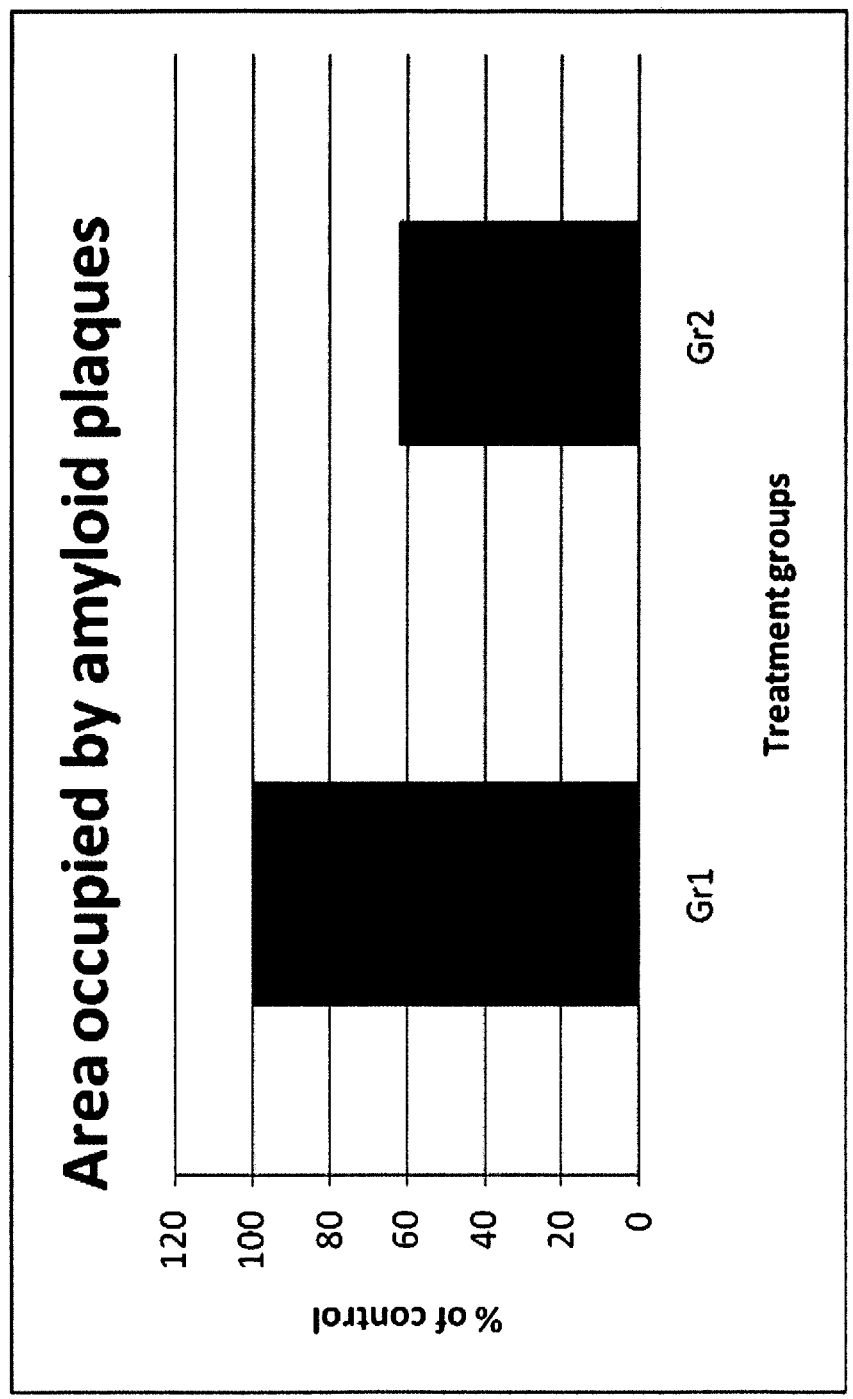

FIG. 10 shows areas occupied by amyloid plaques. Tg2576 were injected 6 times with AFFITOPE vaccines adjuvanted with aluminium hydroxide (ALUM) by s.c. inoculation at monthly intervals. Control mice received PBS-ALUM only. Area occupied by amyloid plaques shown as percent of the control group. Gr1 . . . control group; Gr2 . . . received p4395.

EXAMPLES

Methods

The antibodies used for the mimotope identification according to the present invention detect amino acid sequences derived from human Aβ but do not bind to full length human APP. The sequences detected include EFRHDS (=Original epitope aa3-8 of Aβ), p(E)FRHDS (=Original epitope of the modified aa3-8 of Aβ), EVHHQK (=Original epitope aa11-16 of Aβ). The antibody may be a monoclonal or polyclonal antibody preparation or any antibody part or derivative thereof, the only prerequisite is that the antibody molecule specifically recognises at least one of the epitopes mentioned above (derived from human Aβ), but does not bind to full length human APP.

The mimotopes are identified and further characterised with such monoclonal antibodies and peptide libraries.

Example 1

Generation of Monoclonal Antibodies to Specifically Detect β-Amyloid and N-Terminally Truncated and/or Posttranslationally Modified β-Amyloid Fragments

Example 1a

Generation of Monoclonal Antibody MV-001

A monoclonal antibody derived from the fusion of experiment Alz-5 was generated: In experiment Alz-5 C57/Bl6 mice were immunized repeatedly with original Aβ epitope DAEFRHDSGYC (SEQ ID NO: 89) coupled to KLH (Keyhole Limpet Hemocyanin) and Alum (Aluiminium Hydroxide) as adjuvant. p4371-peptide-specific, antibody-producing hybridomas were detected by ELISA (p1253- and p4371-peptide-coated ELISA plates). Human Aβ40/42 (recombinant protein) was used as positive control peptide: hybridomas recognizing the recombinant protein immobilised on ELISA plates were included because they are binding both peptide and full length Aβ specifically. P1454 (Human Aβ 33-40) was used as negative control peptide. Furthermore hybridomas were tested against p4373. Only hybridomas with no or limited p4373 binding were used for further antibody development.

The Hybridoma clone (MV-001 (internal name 824; IgG1) was purified and analysed for specific detection of p1253, p4371, p4373, p1454 and Aβ respectively. MV-001 recognized the injected epitope (p1253) as well as the specific epitope (p4371) and full length Aβ protein (recombinant protein; obtained from Bachem AG, Bubendorf, Switzerland) in ELISA. It however did not detect p1454 in ELISA. Furthermore, the MV-001 antibodies basically failed to detect the peptide p4373 encoding the pyroglutamate version of Aβ3-10 (30 times lower titer than the original epitopes).

Example 1b

Generation of Monoclonal Antibody MV-003

A monoclonal antibody derived from the fusion of experiment Alz-16 was generated: In experiment Alz-16 BalbC mice were immunized repeatedly with the epitope p(E)FRHDSC (SEQ ID NO: 92) (p4373) coupled to KLH (Keyhole Limpet Hemocyanin) and Alum (Aluiminium Hydroxide) as adjuvant. p4373-peptide-specific, antibody-producing hybridomas were detected by ELISA (p4373-peptide-coated ELISA plates). p1253, p1454 and Aβ40/42 were used as negative control peptides. Furthermore, hybridomas were tested against p4371. Only hybridomas with no or limited p4371 binding were used for further antibody development in order to guarantee for pyroglutamate-specificity.

The Hybridoma clone (MV-003 (internal name D129; IgG1) was purified and analysed for specific detection of p1253, p4371, p4373, p1454 and Aβ respectively. MV-003 recognized the injected epitope (p4373) but failed to detect p1454, p1253 or full length Aβ protein (recombinant protein; obtained from Bachem AG, Bubendorf, Switzerland) in ELISA. Furthermore, the MV-003 antibodies failed to detect the peptide p4371 encoding the normal version of Aβ3-10 (15 times lower titer than the original epitope).

Example 1c

Generation of Monoclonal Antibody MV-004

A monoclonal antibody derived from the fusion of experiment Alz-15 was generated: In experiment Alz-15 BalbC mice were immunized repeatedly with the epitope EVHHQKC (SEQ ID NO: 91) (p4372) coupled to KLH (Keyhole Limpet Hemocyanin) and Alum (Aluiminium Hydroxide) as adjuvant. p4372-peptide-specific, antibody-producing hybridomas were detected by ELISA (p4372-peptide-coated ELISA plates). P4376, p4378, p1454 and Aβ40/42 were used as negative control peptides. Only hybridomas with no or limited p4376 and p4378 binding were used for further antibody development in order to guarantee for specificity against the free N-Terminus at position aa11.

The Hybridoma clone (MV-004 (internal name B204; IgG1) was purified and analysed for specific detection of p4372, p4376, p4378, p1454 and Aβ respectively. MV-004 recognized the injected epitope (p4372) but failed to detect p1454, p4376 and p4378 as well as full length Aβ protein (recombinant protein; obtained from Bachem AG, Bubendorf, Switzerland) in ELISA. The failure to detect p4376, p4378 demonstrates specificity for the free N-terminus at position aa11 in truncated Aβ.

Example 2

Phage Display, In Vitro Binding and Inhibition ELISA

Phage Display libraries used in this example were: Ph.D. 7: New England BioLabs E8102L (linear 7mer library). Phage Display was done according to manufacturer's protocol (www.neb.com).

After 2 or 3 subsequent rounds of panning, single phage clones were picked and phage supernatants were subjected to ELISA on plates coated with the antibody that was used for the panning procedure. Phage clones that were positive in this ELISA (strong signal for the target, but no signal for unspecific control) were sequenced. From DNA sequences, peptide sequences were deduced. These peptides were synthesized and characterised in binding and inhibition ELISA. Additionally, some novel mimotopes were created by combining sequence information from mimotopes identified in the screen to support the identification of a consensus sequence for a mimotope vaccination.

1. In vitro binding assay (ELISA)

Peptides derived from Phage Display as well as variants thereof were coupled to BSA and bound to ELISA plates (1 µM; as indicated in the respective figures) and subsequently incubated with the monoclonal antibody that was used for the screening procedure to analyse binding capacity of identified peptides.

2. In vitro inhibition assay (ELISA)

Different amounts of peptides (concentrations ranging from 10 µg to 0.08 µg; serial dilutions), derived from Phage Display were incubated with the monoclonal antibody that was used for the screening procedure. Peptides diminishing subsequent binding of the antibody to the original epitope coated on ELISA plates were considered as inhibiting in this assay.

Example 3

In Vivo Testing of Mimotopes: Analysis of Immunogenicity and Crossreactivity

1. In Vivo Testing of Mimotopes

Figure 6A:
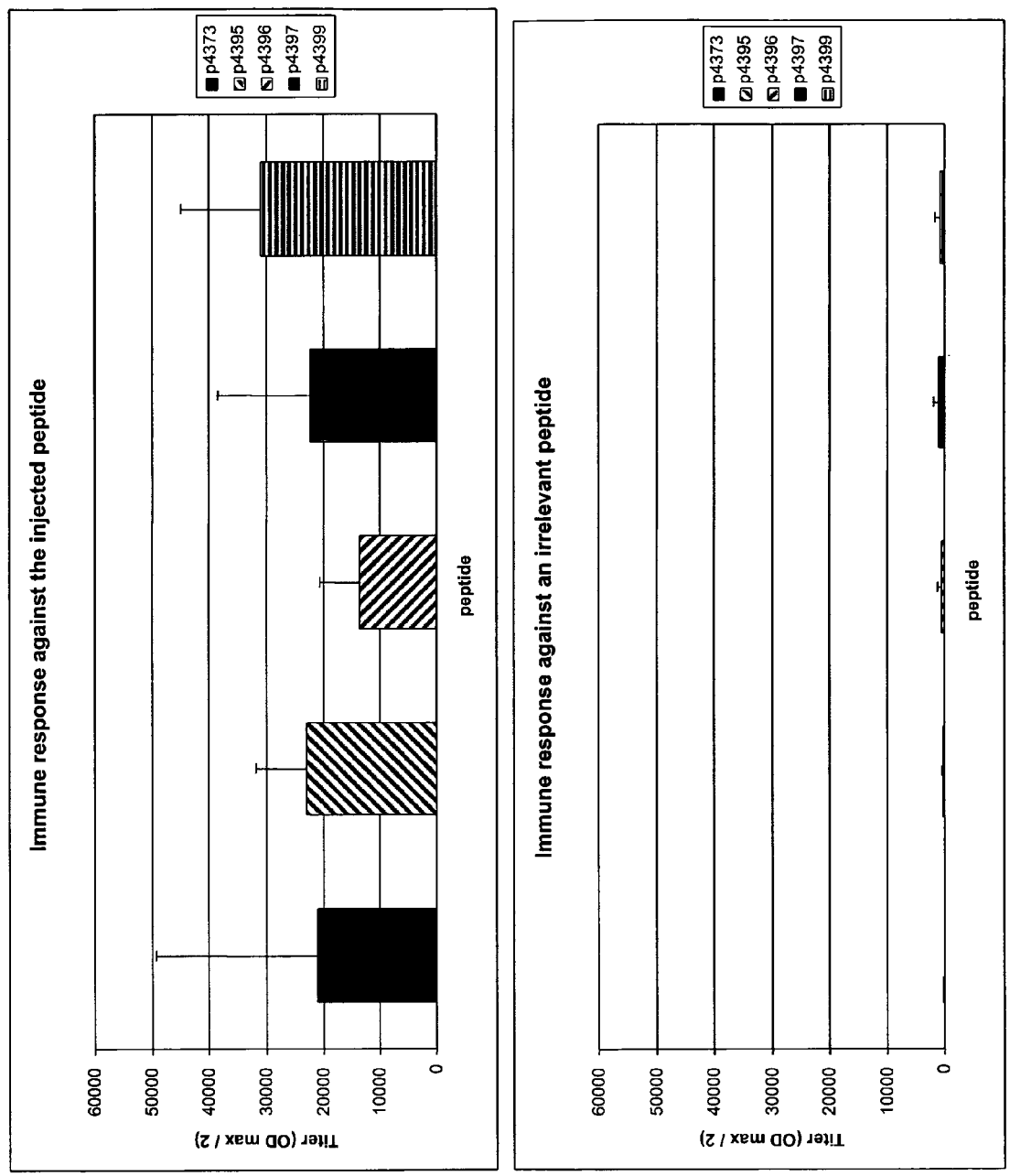
FIG. 6 shows examples for in vivo characterisations of the immune response elicited by mimotope vaccination (injected peptide/irrelevant peptide)

Inhibiting as well as non-inhibiting peptides were coupled to KLH and injected into mice (wildtype C57/Bl6 mice; subcutaneous injection into the flank) together with an appropriate adjuvant (aluminium hydroxide). Animals were vaccinated 3-6 times in biweekly intervals and sera were taken biweekly as well. Titers to injected peptides, as well as to an irrelevant peptide were determined with every serum. Furthermore, titers against the recombinant human Aβ protein, and against original peptides were determined respectively. In general sera were analysed by reaction against peptides coupled to Bovine Serum Albumin (BSA) and recombinant full length proteins which were immobilised on ELISA plates. Titers were determined using anti mouse IgG specific antibodies. For detailed results see FIGS. 6, 7 and 8 respectively.

Figure 1:
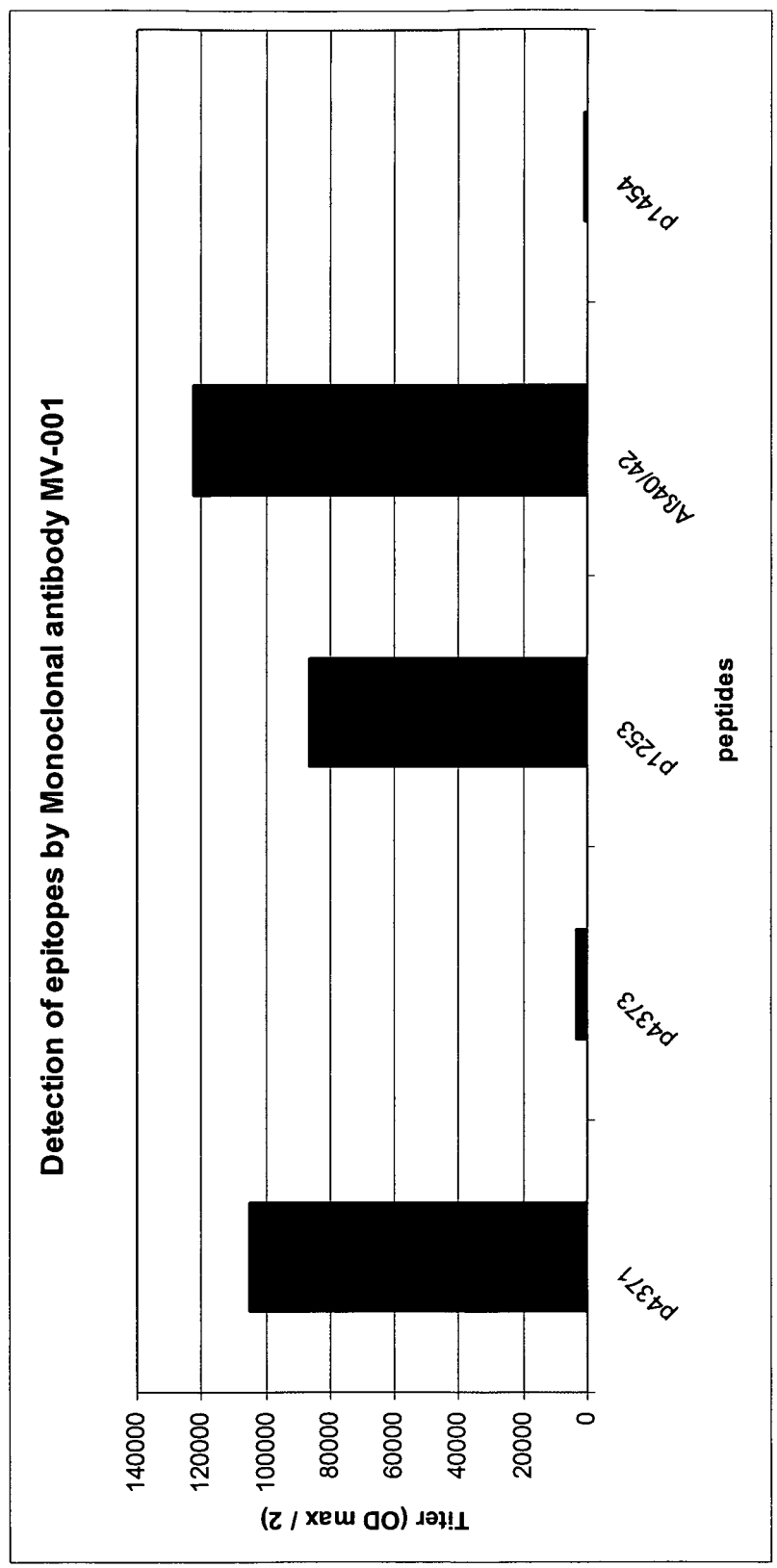
FIG. 1 shows binding of monoclonal antibody MV-001 to specific peptides and recombinant proteins.

2. Results 2.1. Identification of Specific Monoclonal Antibodies (mAB) Directed Against n-Terminally Truncated and Modified Forms of Aβ:

FIG. 1 depicts the characterisation of the monoclonal antibody MV-001 (internal name 824; IgG1) derived from experiment Alz-5 demonstrating specificity for full length Aβ and Aβ truncated at position E3.

Figure 2:
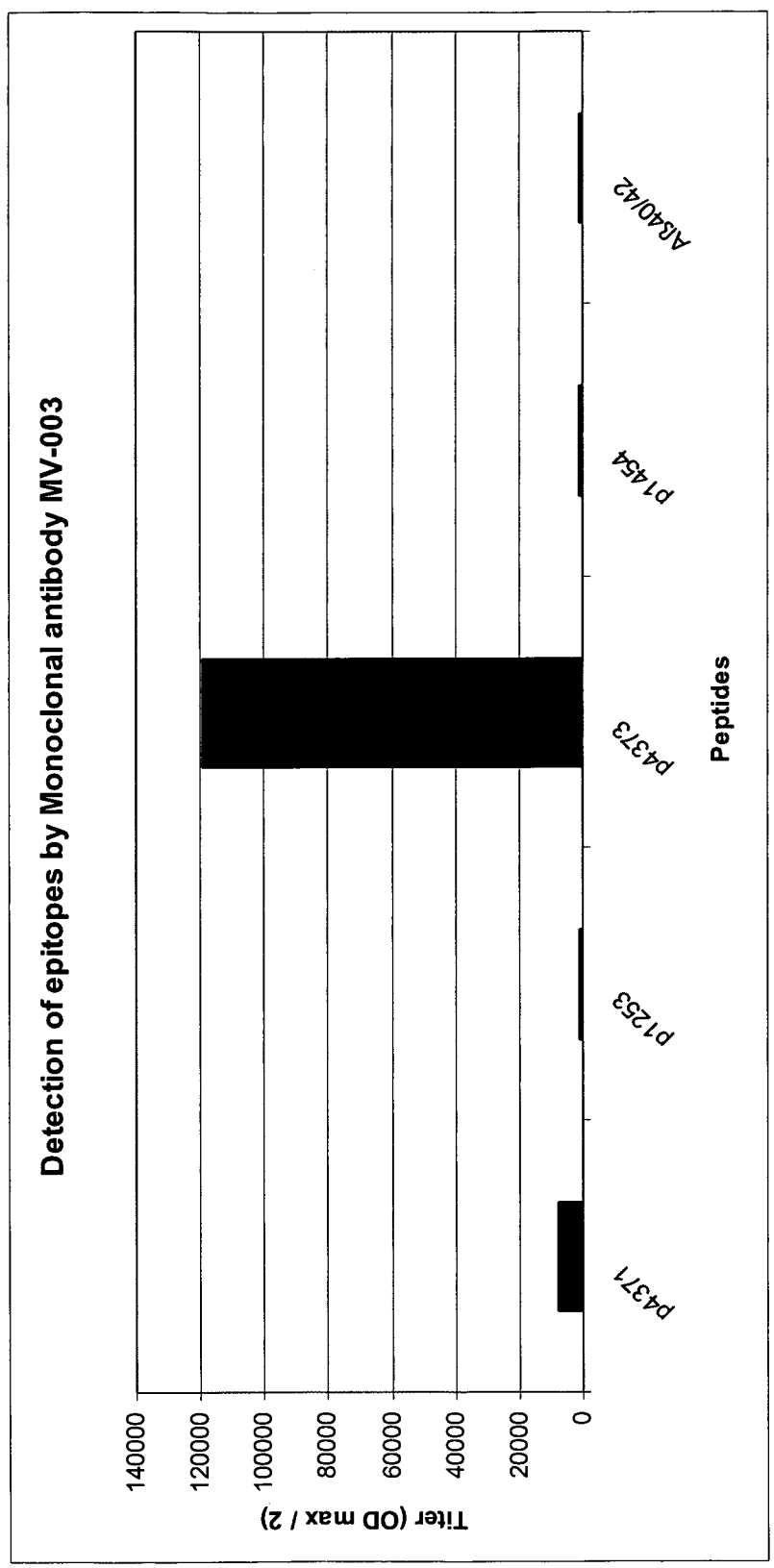
FIG. 2 shows binding of monoclonal antibody MV-003 to specific peptides and recombinant proteins.

FIG. 2 depicts the characterisation of the monoclonal antibody MV-003 (internal name D129; IgG1) derived from experiment Alz-16 demonstrating specificity for Aβ truncated and posttranslationally modified at position p(E)$_3$.

Figure 3:
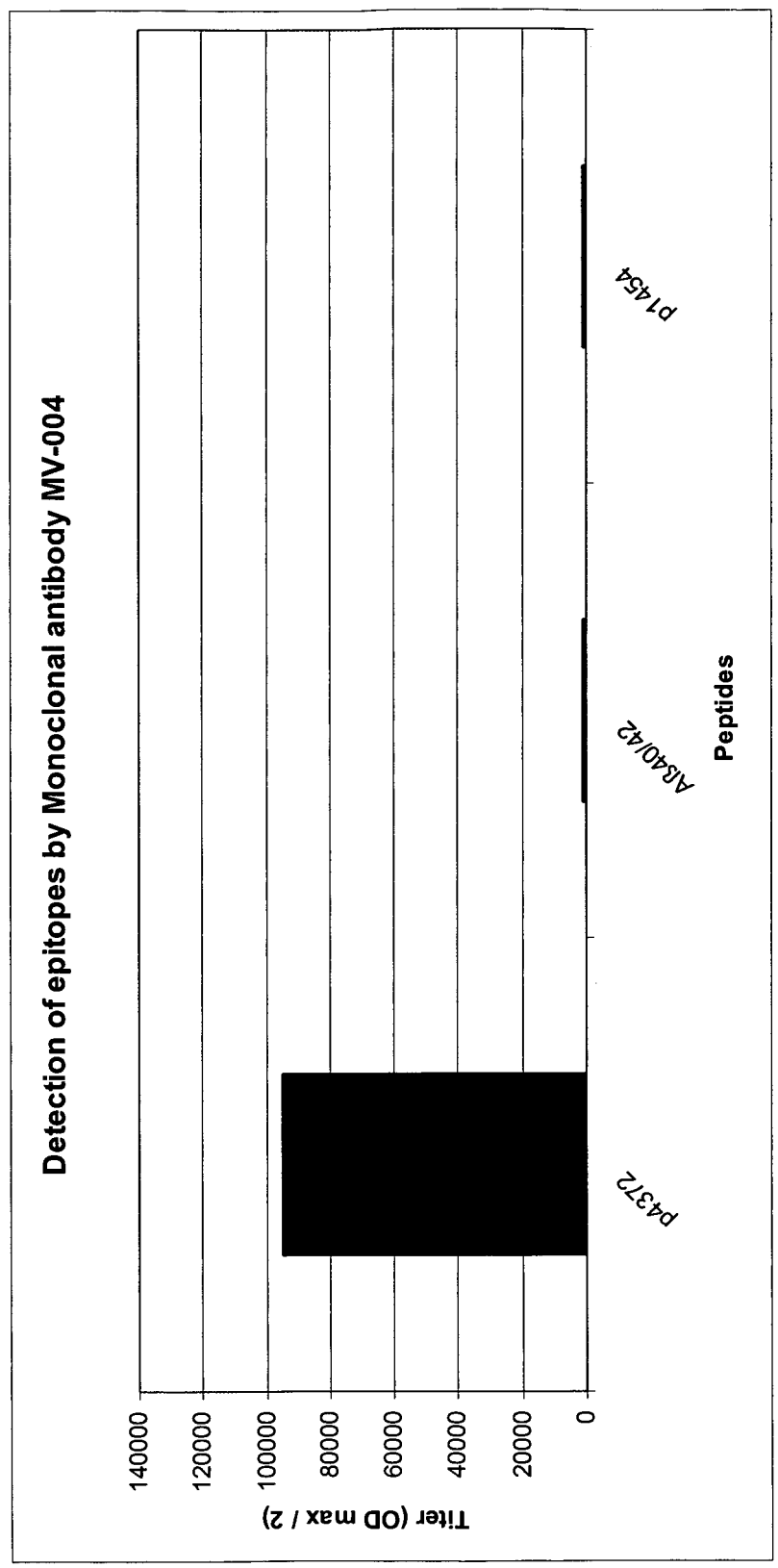
FIG. 3 shows binding of monoclonal antibody MV-004 to specific peptides and recombinant proteins.

FIG. 3 depicts the characterisation of the monoclonal antibody MV-004 (internal name B204; IgG1) derived from experiment Alz-15 demonstrating specificity for Aβ truncated at position E11.

2.2. Screening with Specific mABs Directed Against n-Terminally Truncated and Modified Forms of Aβ:

2.2.1. Phage Display Library Ph.D. 7

2.2.1.1. Screening with Monoclonal Antibody Directed Against p4373

8 Sequences were identified by screening PhD 7 phage display libraries in this screen: Table 1A summarises the peptides identified and their binding capacity as compared to the original epitope.

2.2.1.2. Screening with Monoclonal Antibody Directed Against p4372

9 Sequences were identified by screening PhD 7 phage display libraries in this screen: Table 1B summarises the peptides identified and their binding capacity as compared to the original epitope.

2.2.1.3. Screening with Monoclonal Antibody Directed Against p4371

71 Sequences were identified by screening PhD 7 and PhD12 phage display libraries in this screen: Table 1C summarises the peptides identified and their binding capacity as compared to the original epitope.

TABLE 1A mimotopes binding to the parental antibody MV-003

| Internal Peptide number | SEQ ID No. | Sequence | Binding Capacity |
|---|---|---|---|
| p4395 | 1 | IRWDTPC | 2 |
| p4396 | 2 | VRWDVYPC | 1 |
| p4397 | 3 | IRYDAPLC | 1 |
| p4399 | 4 | IRYDMAGC | 1 |
| p4728 | 5 | IRWDTSLC | 3 |
| p4756 | 6 | IRWDQPC | 3 |
| p4792 | 7 | IRWDGC | 1 |
| p4793 | 8 | IRWDGGC | 2 |

Legend to Table 1A: the binding capacity is coded by the following binding code: 1:X describes the dilution factor of the parental AB.

| binding code | | OD halfmax 1:X |
|---|---|---|
| 0 | no binding | :0 |
| 1 | weak binding | :<16000 |
| 2 | medium binding | :16-60000 |
| 3 | strong binding | :>60000 |

TABLE 1B mimotopes binding to the parental antibody MV-004

| Internal Peptide number | SEQ ID No. | Sequence | Binding Capacity |
|---|---|---|---|
| p4417 | 9 | EVWHRHQC | 2 |
| p4418 | 10 | ERWHEKHC | 3 |
| p4419 | 11 | EVWHRLQC | 3 |
| p4420 | 12 | ELWHRYPC | 2 |
| p4665 | 13 | ELWHRAFC | 2 |
| p4786 | 14 | ELWHRAC | 1 |
| p4788 | 15 | EVWHRGC | 1 |
| p4789 | 16 | EVWHRHC | 1 |
| p4790 | 17 | ERWHEKC | 1 |

Legend to Table 1B: the binding capacity is coded by the following binding code: 1:X describes the dilution factor of the parental AB.

| binding code | | OD halfmax 1:X |
|---|---|---|
| 0 | no binding | :0 |
| 1 | weak binding | :<24000 |
| 2 | medium binding | :24-96000 |
| 3 | strong binding | :>96000 |

TABLE 1C mimotopes binding to the parental antibody MV-001

| Internal Peptide number | SEQ ID No. | Sequence | Binding Capacity |
|---|---|---|---|
| p4380 | 18 | QDFRHYC | 2 |
| p4381 | 19 | SEFKHGC | 3 |
| p4382 | 20 | TSFRHGC | 2 |
| p4383 | 21 | TSVFRHC | 3 |
| p4384 | 22 | TPFRHTC | 2 |
| p4385 | 23 | SQFRHYC | 2 |
| p4386 | 24 | LMFRHNC | 3 |
| p4387 | 25 | SAFRHHC | 2 |
| p4388 | 26 | LPFRHGC | 2 |
| p4389 | 27 | SHFRHGC | 2 |
| p4390 | 28 | ILFRHGC | 3 |
| p4391 | 29 | QFKHDLC | 2 |
| p4392 | 30 | NWFPHPC | 1 |
| p4393 | 31 | EEFKYSC | 2 |
| p4701 | 32 | NELRHSTC | 3 |
| p4702 | 33 | GEMRHQPC | 3 |
| p4703 | 34 | DTYFPRSC | 2 |
| p4704 | 35 | VELRHSRC | 2 |
| p4705 | 36 | YSMRHDAC | 2 |
| p4706 | 37 | AANYFPRC | 2 |
| p4707 | 38 | SPNQFRHC | 3 |
| p4708 | 39 | SSSFFPRC | 2 |
| p4709 | 40 | EDWFFWHC | 1 |
| p4710 | 41 | SAGSFRHC | 3 |
| p4711 | 42 | QVMRHHAC | 2 |
| p4712 | 43 | SEFSHSSC | 3 |
| p4713 | 44 | QPNLFYHC | 1 |
| p4714 | 45 | ELFKHHLC | 3 |
| p4715 | 46 | TLHEFRHC | 3 |
| p4716 | 47 | ATFRHSPC | 2 |
| p4717 | 48 | APMYFPHC | 2 |
| p4718 | 49 | TYFSHSLC | 2 |
| p4719 | 50 | HEPLFSHC | 1 |
| p4721 | 51 | SLMRHSSC | 2 |
| p4722 | 52 | EFLRHTLC | 3 |
| p4723 | 53 | ATPLFRHC | 3 |

TABLE 1C-continued

| Internal Peptide number | SEQ ID No. | Sequence | Binding Capacity |
|---|---|---|---|
| p4724 | 54 | QELKRYYC | 1 |
| p4725 | 55 | THTDFRHC | 3 |
| p4726 | 56 | LHIPFRHC | 3 |
| p4727 | 57 | NELFKHFC | 2 |
| p4729 | 58 | SQYFPRPC | 2 |
| p4730 | 59 | DEHPFRHC | 3 |
| p4731 | 60 | MLPFRHGC | 2 |
| p4732 | 61 | SAMRHSLC | 2 |
| p4733 | 62 | TPLMFWHC | 1 |
| p4734 | 63 | LQFKHSTC | 2 |
| p4735 | 64 | ATFRHSTC | 2 |
| p4736 | 65 | TGLMFKHC | 2 |
| p4737 | 66 | AEFSHWHC | 2 |
| p4738 | 67 | QSEFKHWC | 3 |
| p4739 | 68 | AEFMHSVC | 2 |
| p4740 | 69 | ADHDFRHC | 3 |
| p4741 | 70 | DGLLFKHC | 3 |
| p4742 | 71 | IGFRHDSC | 2 |
| p4743 | 72 | SNSEFRRC | 3 |
| p4744 | 73 | SELRHSTC | 3 |
| p4745 | 74 | THMEFRRC | 3 |
| p4746 | 75 | EELRHSVC | 3 |
| p4747 | 76 | QLFKHSPC | 3 |
| p4748 | 77 | YEFRHAQC | 3 |
| p4749 | 78 | SNFRHSVC | 3 |
| p4750 | 79 | APIQFRHC | 3 |
| p4751 | 80 | AYFPHTSC | 2 |
| p4752 | 81 | NSSELRHC | 3 |
| p4753 | 82 | TEFRHKAC | 3 |
| p4754 | 83 | TSTEMWHC | 1 |
| p4755 | 84 | SQSYFKHC | 3 |
| p4800 | 85 | CSEFKH | 3 |
| p4801 | 86 | SEFKHC | 3 |
| p4802 | 87 | CHEFRH | 3 |
| p4803 | 88 | HEFRHC | 3 |

Legend to Table 1C: the binding capacity is coded by the following binding code: 1:X describes the dilution factor of the parental AB

| binding code | | OD halfmax 1:X |
|---|---|---|
| 0 | no binding | :0 |
| 1 | weak binding | :<4000 |

TABLE 1C-continued

| | | |
|---|---|---|
| 2 | medium binding | :4000-20000 |
| 3 | strong binding | :>20000 |

Figure 4A:
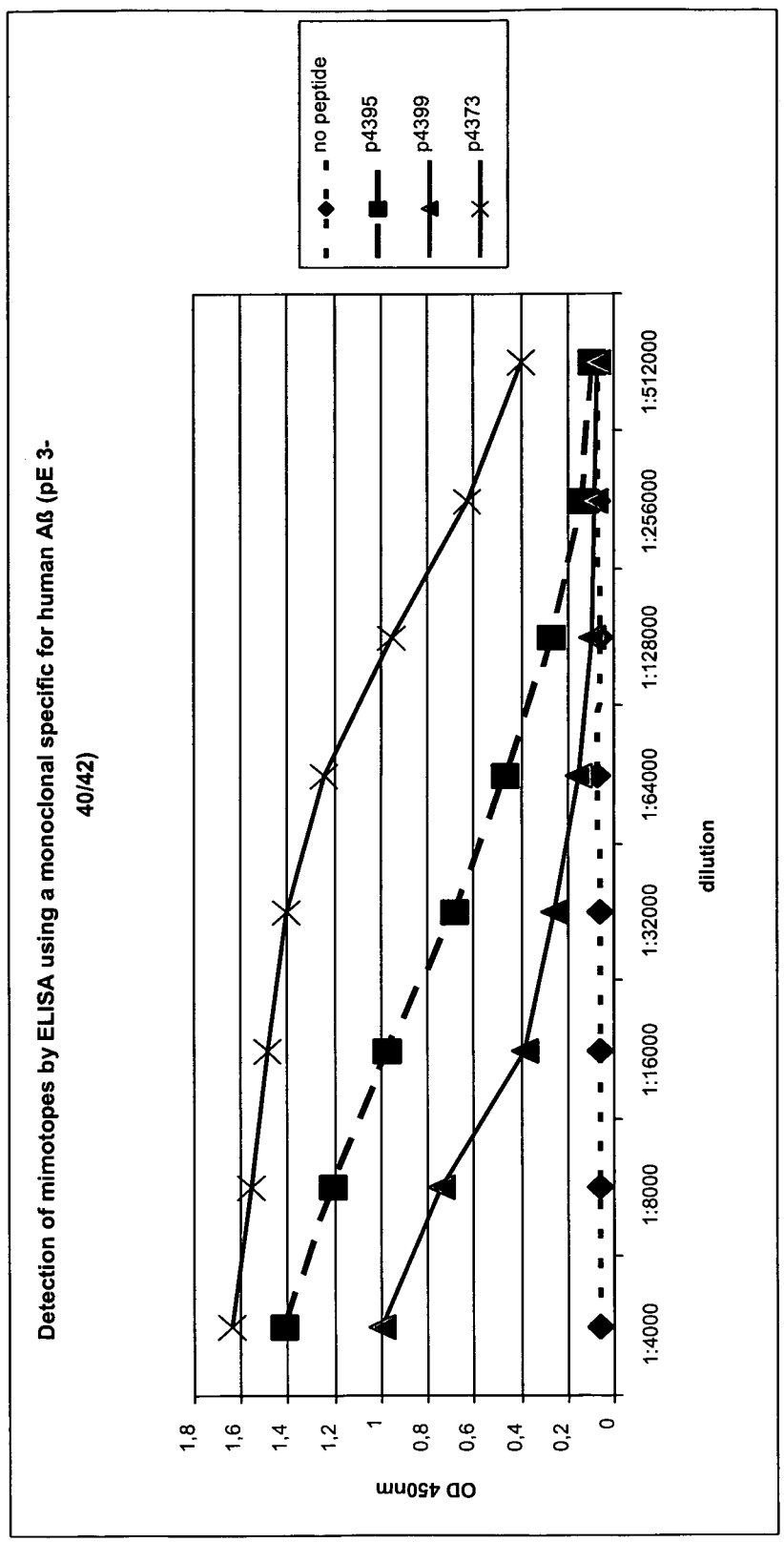
FIG. 4 shows typical binding assays with mimotopes for β-amyloid and N-terminally truncated and/or posttranslationally modified β-amyloid fragments.
Figure 4B:
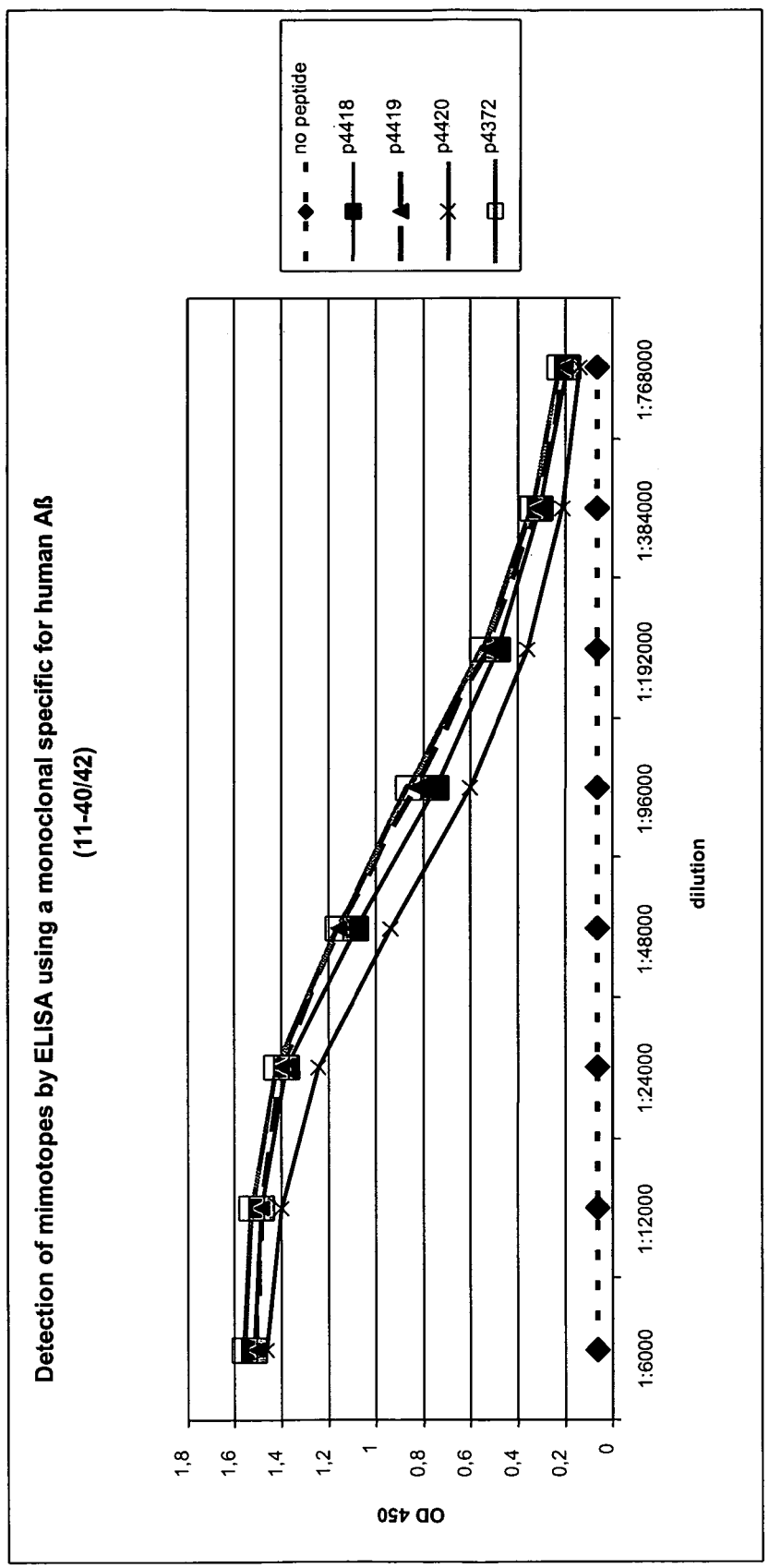
Figure 4C:
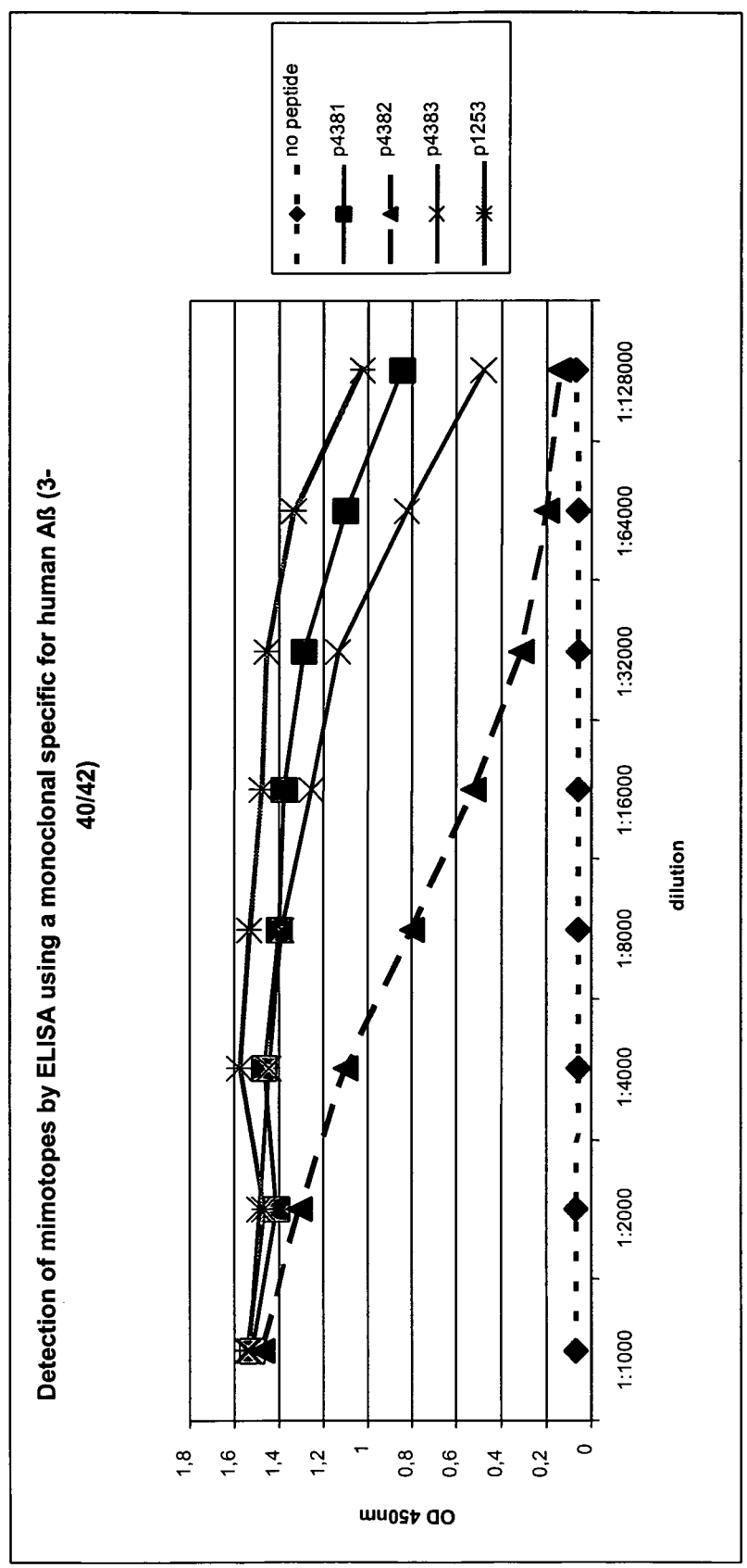
Figure 5A:
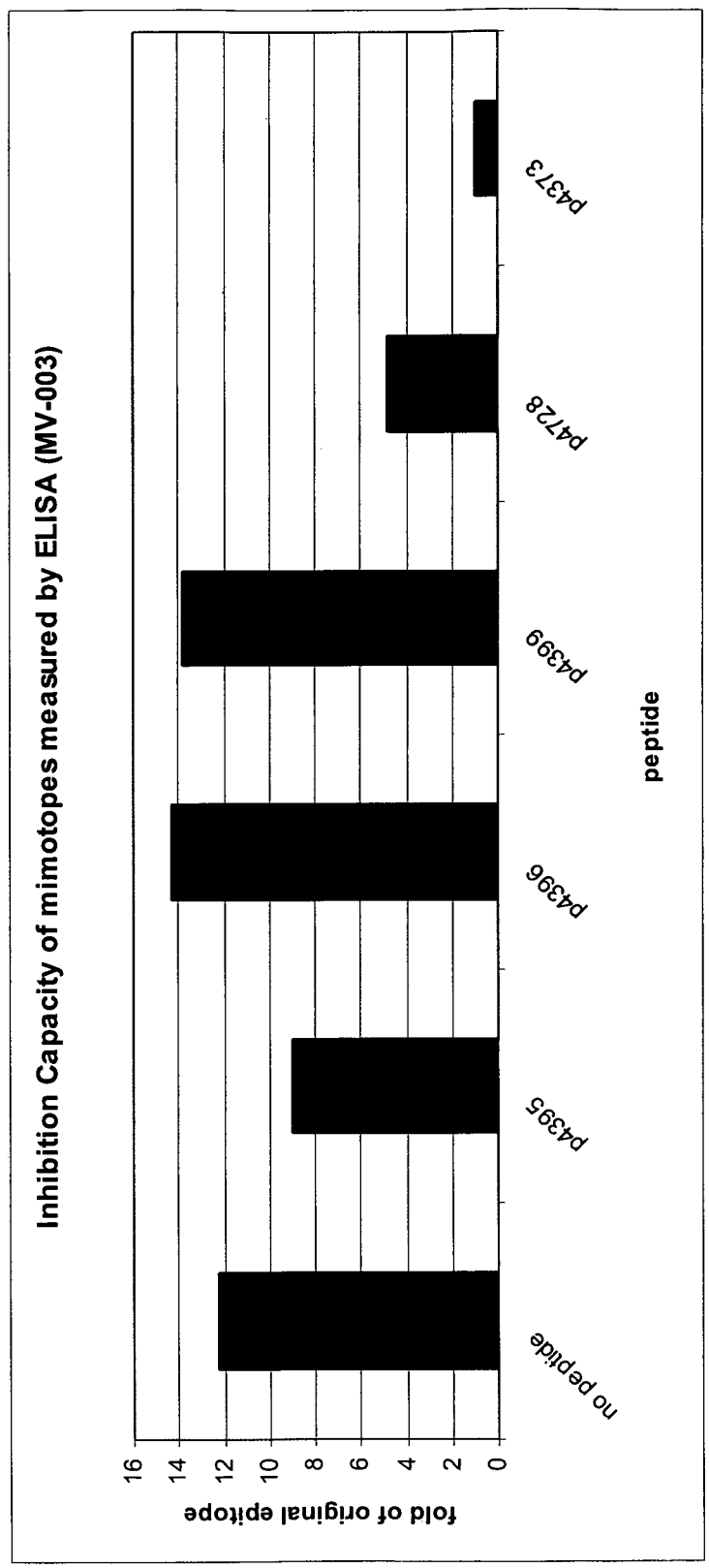
FIG. 5 shows typical inhibition assays with mimotopes for β-amyloid and N-terminally truncated and/or posttranslationally modified β-amyloid fragments.
Figure 5B:
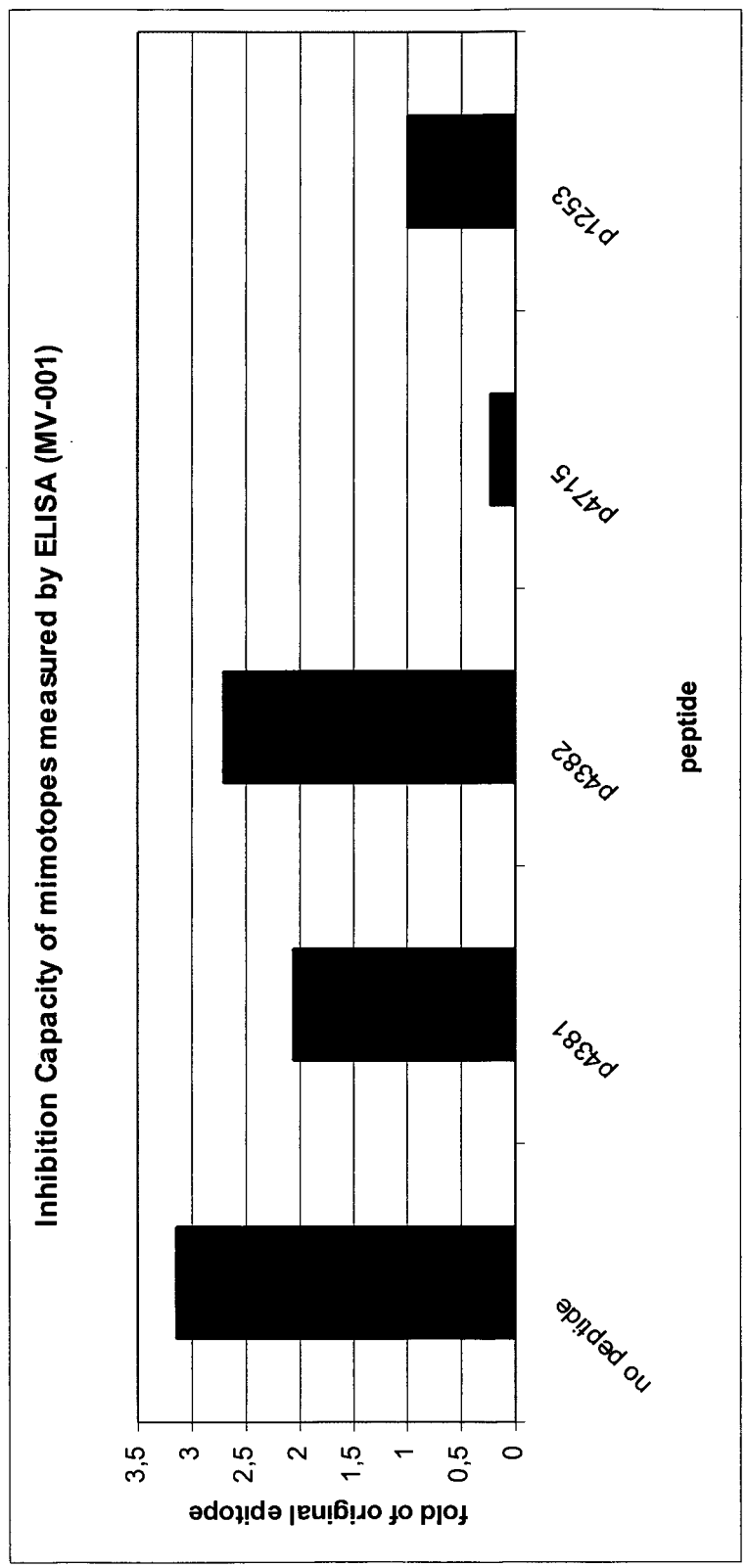
Figure 5C:
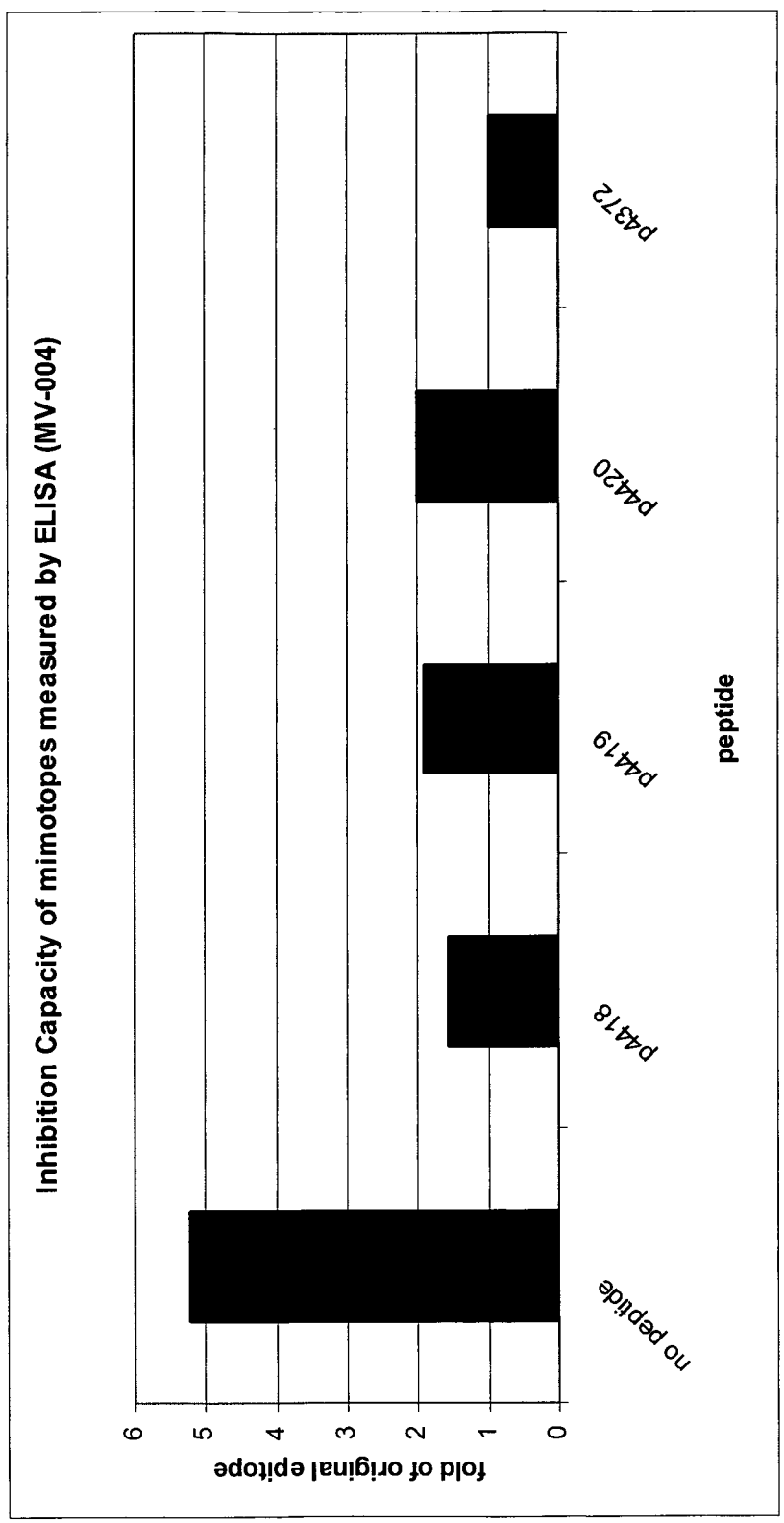

2.3. In Vitro Characterisation of Mimotopes Identified in Screening Phage Display Libraries with Monoclonal Antibodies Directed Against n-Terminally Truncated and Modified Forms of Aβ:

FIGS. 4 and 5 show representative examples for binding and inhibition assays used to characterise mimotopes in vitro. Data obtained are summarised in Tables 1 and 2 respectively.

MV-003 Mimotopes: From the 8 sequences presented 6 sequences inhibit binding of the p(E)3-7Aβ specific monoclonal antibody in in vitro competition experiments: Additional 2 sequences were identified that do not inhibit binding of monoclonal antibody in in vitro competition experiments but still retain binding capacity to the parental antibody (Table 2A).

MV-004 Mimotopes: All the 9 sequences presented inhibit binding of the monoclonal antibody specifically binding the free N-terminus of Aβ truncated at position E11 in in vitro competition experiments: (Table 2B).

MV-001 Mimotopes: From the 71 sequences presented 27 sequences inhibit binding of the monoclonal antibody specifically directed against Aβ truncated at position E3 in in vitro competition experiments: Additional 44 sequences were identified that do not inhibit binding of monoclonal antibody in in vitro competition experiments but still retain binding capacity to the parental antibody (Table 2C).

Table 2: mimotopes identified in this invention giving positive results in inhibiting assays

TABLE 2A

MV-003 Mimotopes

| Internal Peptide number | SEQ ID No. | Sequence | Inhibition Capacity |
|---|---|---|---|
| p4395 | 1 | IRWDTPC | 1 |
| p4397 | 3 | IRYDAPLC | 1 |
| p4728 | 5 | IRWDTSLC | 2 |
| p4756 | 6 | IRWDQPC | 1 |
| p4792 | 7 | IRWDGC | 1 |
| p4793 | 8 | IRWDGGC | 1 |

Legend to Table 2A: the inhibition capacity is coded by the following code: Weak inhibition means more peptide is required to lower AB binding than with the original epitope; strong inhibition means similar peptide amounts are required for mimotope and original epitope for lowering AB binding. Mimotopes are compared to the original peptide as standard. OD at 10 µg peptide used in the assay is used to calculate the competition capacity compared to original peptide.

| competition code | |
|---|---|
| 0 | no inhibition (OD of 10 µg peptide above 12 times of original peptide) |
| 1 | Weaker than original epitope (OD of 10 µg peptide below 12 times of original peptide) |
| 2 | strong inhibition (as original epitope; OD of 10 µg peptide below 5 times of original peptide) |

TABLE 2B

MV-004 Mimotopes

| Internal Peptide number | SEQ ID No. | Sequence | Inhibition Capacity |
|---|---|---|---|
| p4417 | 9 | EVWHRHQC | 1 |
| p4418 | 10 | ERWHEKHC | 2 |
| p4419 | 11 | EVWHRLQC | 2 |
| p4420 | 12 | ELWHRYPC | 1 |
| p4665 | 13 | ELWHRAFC | 2 |
| p4786 | 14 | ELWHRAC | 1 |
| p4788 | 15 | EVWHRGC | 1 |
| p4789 | 16 | EVWHRHC | 1 |
| p4790 | 17 | ERWHEKC | 2 |

Legend to Table 2B: the inhibition capacity is coded by the following code: Weak inhibition means more peptide is required to lower AB binding than with the original epitope; strong inhibition means similar peptide amounts are required for mimotope and original epitope for lowering AB binding. Mimotopes are compared to the original peptide as standard. OD at 10 µg peptide used in the assay is used to calculate the competition capacity compared to original peptide.

| competition code | |
|---|---|
| 0 | no inhibition (OD of 10 µg peptide above 5 times of original peptide) |
| 1 | Weaker than original epitope (OD of 10 µg peptide below 5 times of original peptide) |
| 2 | strong inhibition (as original epitope; OD of 10 µg peptide below 2 times of original peptide) |

TABLE 2C

MV-001 Mimotopes

| Internal Peptide number | SEQ ID No. | Sequence | Inhibition Capacity |
|---|---|---|---|
| p4380 | 18 | QDFRHYC | 1 |
| p4381 | 19 | SEFKHGC | 1 |
| p4382 | 20 | TSFRHGC | 1 |
| p4383 | 21 | TSVFRHC | 1 |

TABLE 2C-continued

| | | | |
|---|---|---|---|
| p4384 | 22 | TPFRHTC | 1 |
| p4385 | 23 | SQFRHYC | 1 |
| p4386 | 24 | LMFRHNC | 1 |
| p4387 | 25 | SAFRHHC | 1 |
| p4388 | 26 | LPFRHGC | 1 |
| p4389 | 27 | SHFRHGC | 1 |
| p4390 | 28 | ILFRHGC | 1 |
| p4391 | 29 | QFKHDLC | 1 |
| p4392 | 30 | NWFPHPC | 1 |
| p4393 | 31 | EEFKYSC | 1 |
| p4707 | 38 | SPNQFRHC | 1 |
| p4715 | 46 | TLHEFRHC | 2 |
| p4725 | 55 | THTDFRHC | 1 |
| p4730 | 59 | DEHPFRHC | 1 |
| p4738 | 67 | QSEFKHWC | 1 |
| p4740 | 69 | ADHDFRHC | 1 |
| p4741 | 70 | DGLLFKHC | 1 |
| p4746 | 75 | EELRHSVC | 1 |
| p4753 | 82 | TEFRHKAC | 2 |
| p4800 | 85 | CSEFKH | 2 |
| p4801 | 86 | SEFKHC | 1 |
| p4802 | 87 | CHEFRH | 2 |
| p4803 | 88 | HEFRHC | 2 |

Legend to Table 2C: the inhibition capacity is coded by the following code: Weak inhibition means more peptide is required to lower AB binding than with the original epitope; strong inhibition means similar peptide amounts are required for mimotope and original epitope for lowering AB binding. Mimotopes are compared to the original peptide as standard. OD at 10 μg peptide used in the assay is used to calculate the competition capacity compared to original peptide.

| competition code | |
|---|---|
| 0 | no inhibition (OD of 10 μg peptide above 3 times of original peptide) |
| 1 | Weaker than original epitope (OD of 10 μg peptide below 3 times of original peptide) |
| 2 | strong inhibition (as original epitope; OD of 10 μg peptide below 2 times of original peptide) |

TABLE 3

Non-mimotope peptides

| Internal Peptide number | SEQ ID No. | Sequence |
|---|---|---|
| p1253 | 89 | DAEFRHDSGYC |
| p4371 | 90 | EFRHDS-C |
| p4372 | 91 | EVHHQK-C |
| p4373 | 92 | p(E)FRHDS-C |
| p4374 | 93 | p(E)VHHQKLVFC |
| p4376 | 94 | GYEVHHQKC |
| p4377 | 95 | EVHHQKLVFC |
| p4378 | 96 | C-EVHHQKLVFF |
| p1454 | 97 | CGLMVGGVV |
| A81-40 | 98 | DAEFRHDSGYEVHHQKLVFFAEDVGSNKGAI-IGLMVGGVV |
| A81-42 | 99 | DAEFRHDSGYEVHHQKLVFFAEDVGSNKGAI-IGLMVGGVVIA |
| sAPPalpha | 100 | alpha-Secretase induced cleavage product derived from human APP (gi: 112927) |

2.4. In Vivo Characterisation of Mimotopes Identified in Screening Phage Display Libraries with a Monoclonal Antibody Directed Against Against n-Terminally Truncated and Modified Forms of Aβ:

Female C57/bl6 mice, 5-6 mice per group, were subcutaneously immunized with 30 μg peptide coupled to KLH. Control groups were administered original epitope-KLH conjugates respectively. As adjuvant alum was used (always 1 mg per mouse). The peptides administered were all able to bind to monoclonal antibodies specifically although some of the peptides did not inhibit the binding of the original epitope to its parental antibody in vitro (in an in vitro inhibition assay). The in vitro ELISA assay to determine the antibody titer was performed with sera of single mice after each vaccination in a two week interval (see FIGS. 6 and 7 respectively). The wells of the ELISA plate were coated with mimotope-BSA conjugate and an irrelevant peptide-BSA conjugate (negative control). The positive control was performed by reaction of the parental antibody with the respective mimotope-BSA conjugate. The detection was performed with anti-mouse IgG. Additionally, recombinant proteins were immobilised on ELISA plates and sera reacted accordingly. FIGS. 6 to 8 show representative examples for assays used to characterise mimotopes in vivo.

FIG. 6 shows examples for in vivo characterisations of the immune response elicited by mimotope vaccination by analysing the immune response against injected peptide and an irrelevant peptide, containing an unrelated sequence. In all three examples shown, the original epitopes and the mimotopes, elicit immune responses against the injected peptides but fail to induce a relevant immune response against an unrelated sequence (p1454).

As example for MV-003-mimotopes, original epitope p4373 and the mimotopes p4395, p4396, p4397, and p4399 are depicted in FIG. 6A. All vaccines are mounting similar immune responses against their respective mimotopes. Neither original epitope p4373-vaccine treated nor the animals treated with mimotope p4395, p4396, p4397 or p4399-vaccines mount relevant titers against irrelevant peptide p1454 (11×-25× less than injected peptides).

Figure 6B:
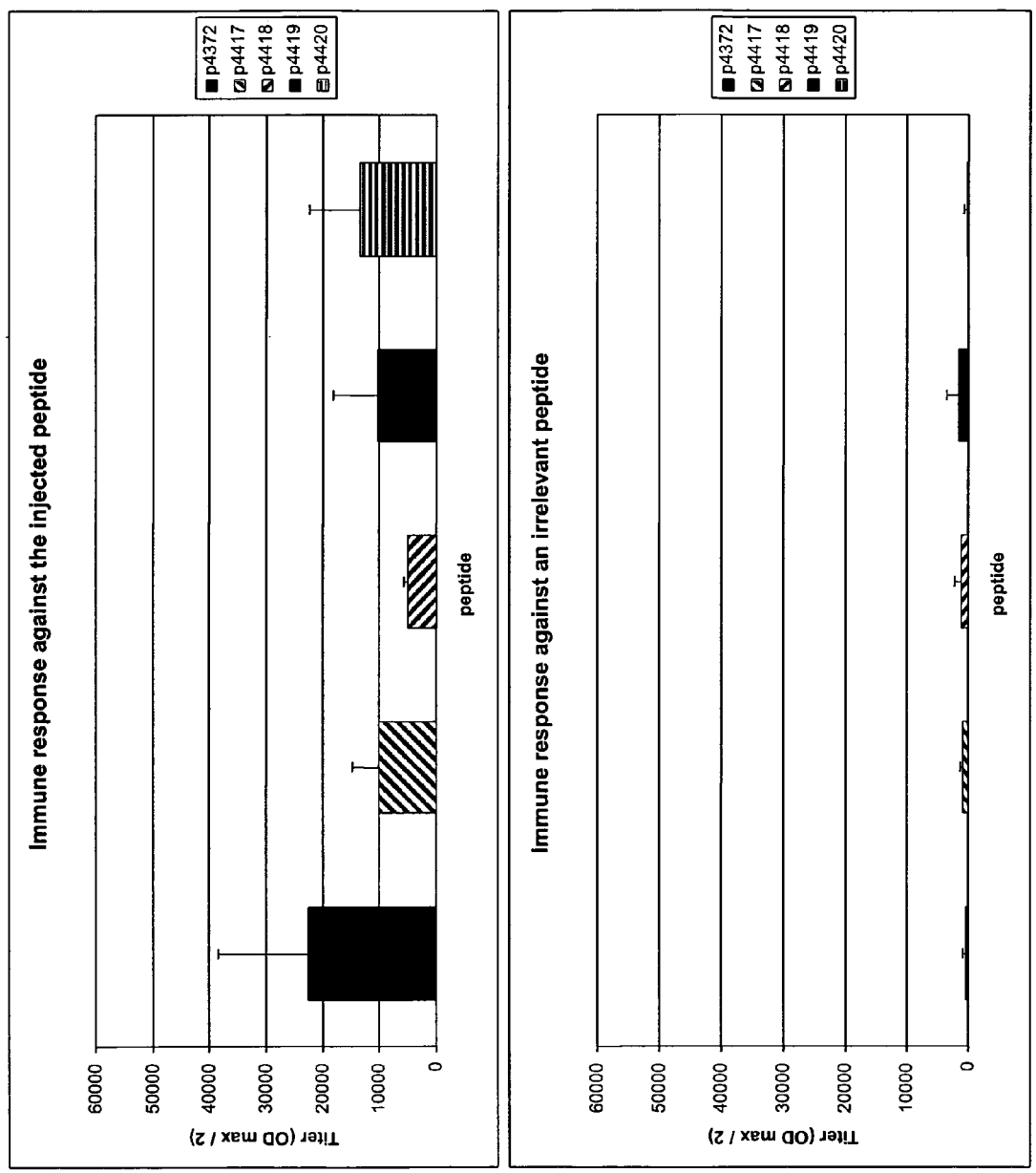

As example for MV-004-mimotopes original epitope p4372 and the mimotopes p4417, p4418, p4419, and p4420 are depicted in FIG. 6B. All vaccines are mounting similar immune responses against their respective mimotopes. Neither original epitope p4372-vaccine treated nor the animals treated with mimotope p4417, p4418, p4419, and p4420-vaccines mount relevant titers against irrelevant peptide p1454 (20-80× less than injected peptides).

Figure 6C:
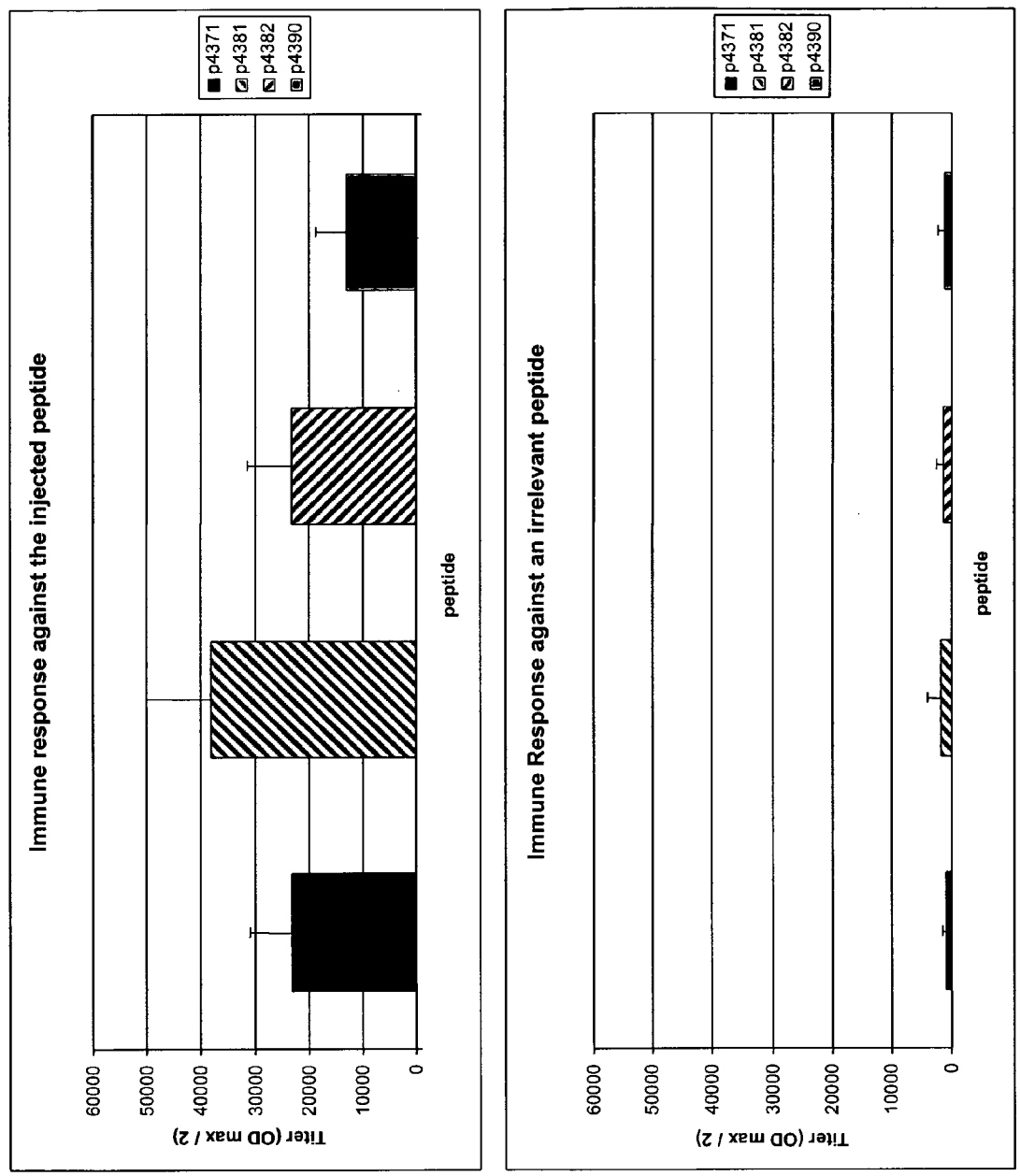

As example for MV-001-mimotopes original epitope p4371 and the mimotopes p4381, p4382, and p4390 are depicted in FIG. 6C. All vaccines are mounting similar immune responses against their respective mimotopes. Neither original epitope p4371-vaccine treated nor the animals treated with mimotope p4381, p4382, and p4390-vaccines mount relevant titers against irrelevant peptide p1454 (>10× less than injected peptides).

FIG. 7 shows examples for in vivo characterisations of the immune response elicited by mimotope vaccination against the respective original epitope of the parental antibody as well as against peptides derived of other forms of truncated species of Aβ.

Figure 7A:
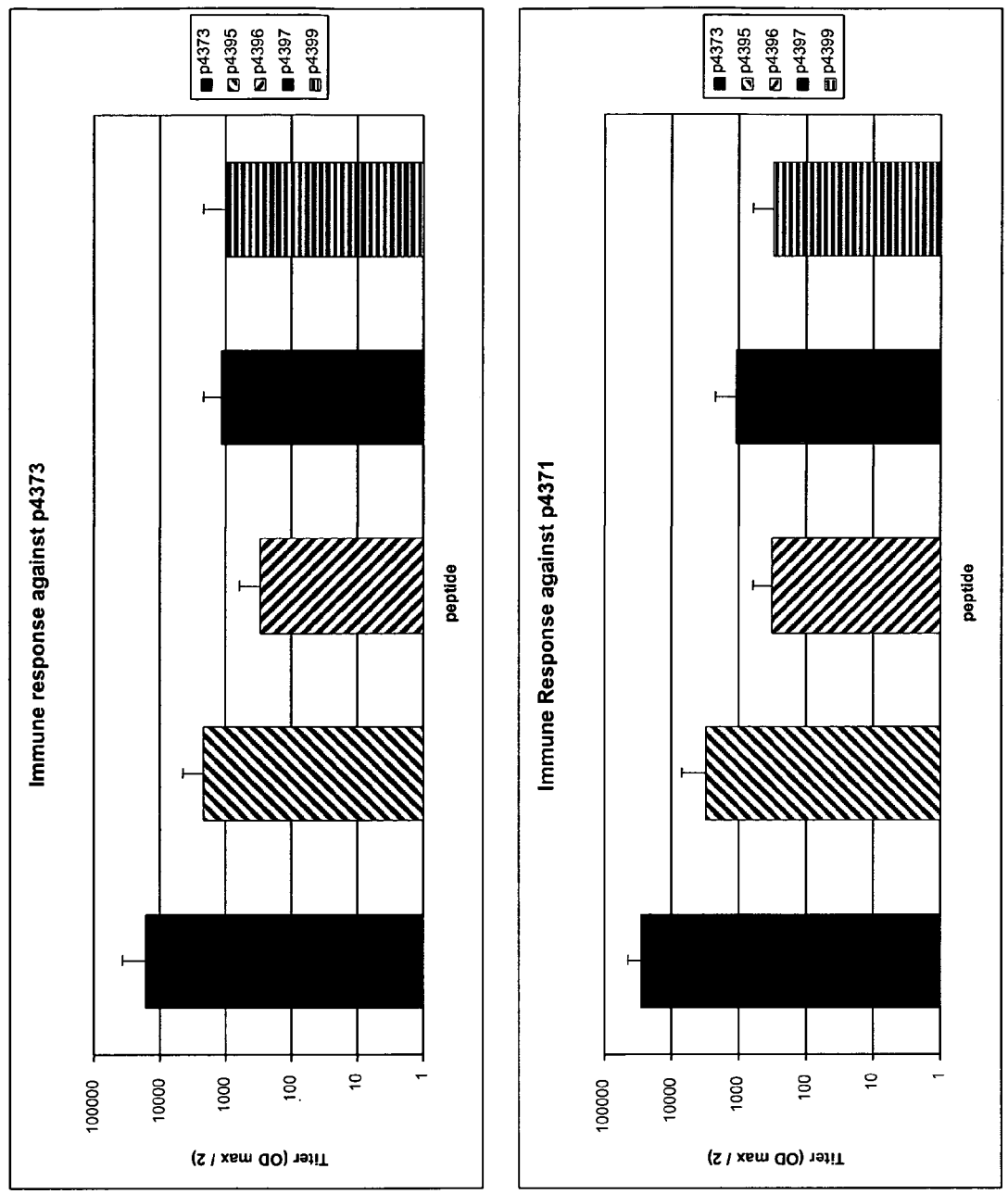
FIG. 7 shows examples for in vivo characterisation of the immune response elicited by mimotope vaccination against Amyloid Beta fragments.

As example for MV-003-mimotopes, original epitope p4373 and the mimotopes p4395, p4396, p4397, and p4399 are depicted in FIG. 7A. 3/4 Mimotope vaccines indicated mount detectable immune responses against the original epitope p4373. A similar phenomenon can be detected analysing cross reactivity against the non-modified form as displayed by p4371. The original epitope p4373-vaccine and 2/4 Mimotope vaccines mount relevant titers against p4371. Surprisingly, the mimotopes selected by MV-003, which is specifically binding to p4373 are also inducing a immune reaction cross reacting with the unmodified form of the original epitope.

Figure 7B:
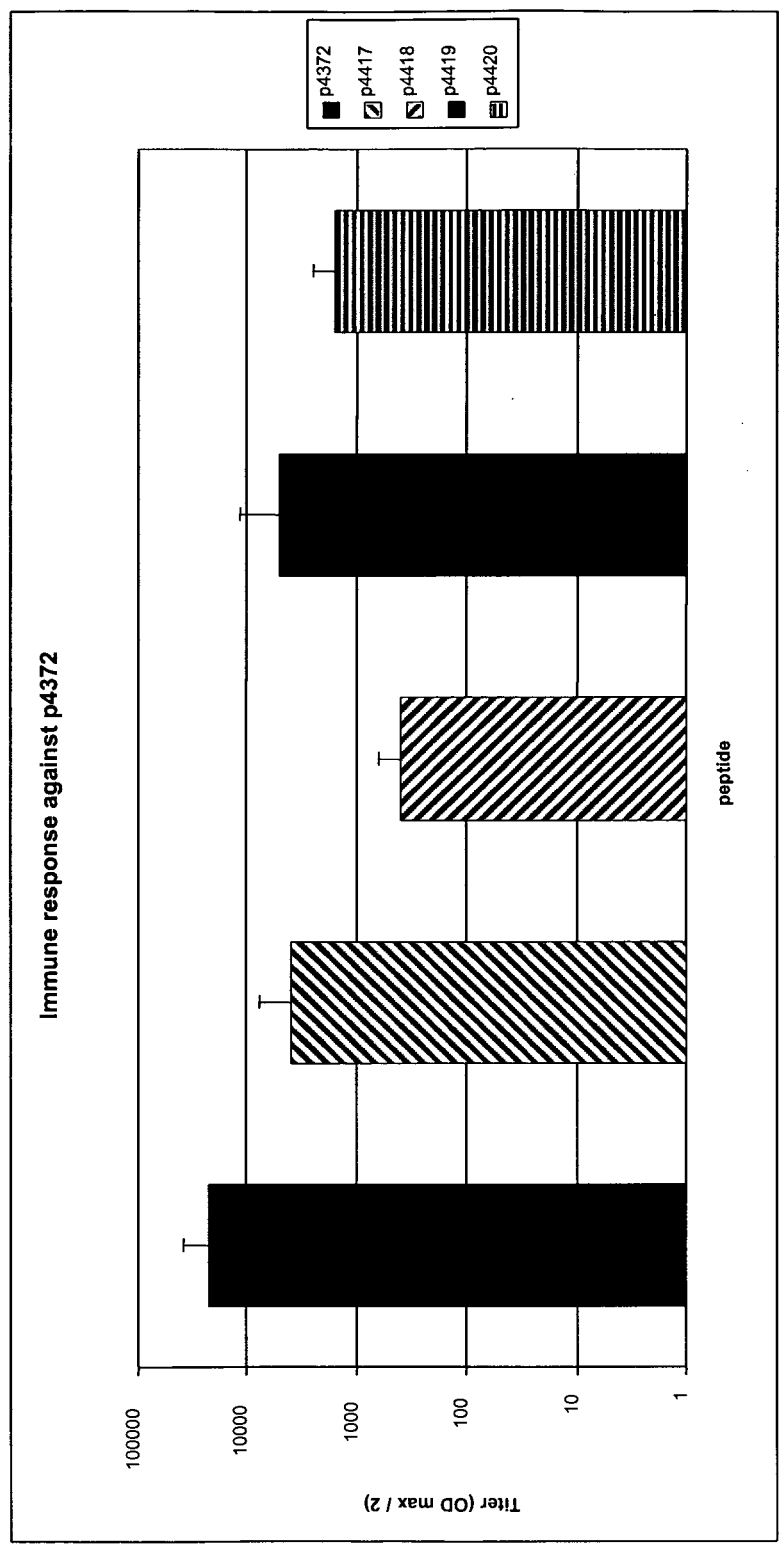

As example for MV-004-mimotopes, original epitope p4372 and the mimotopes p4417, p4418, p4419, and p4420 are depicted in FIG. 7B. 3/4 Mimotope vaccines shown mount detectable immune responses against the original epitope p4372.

Figure 7C:
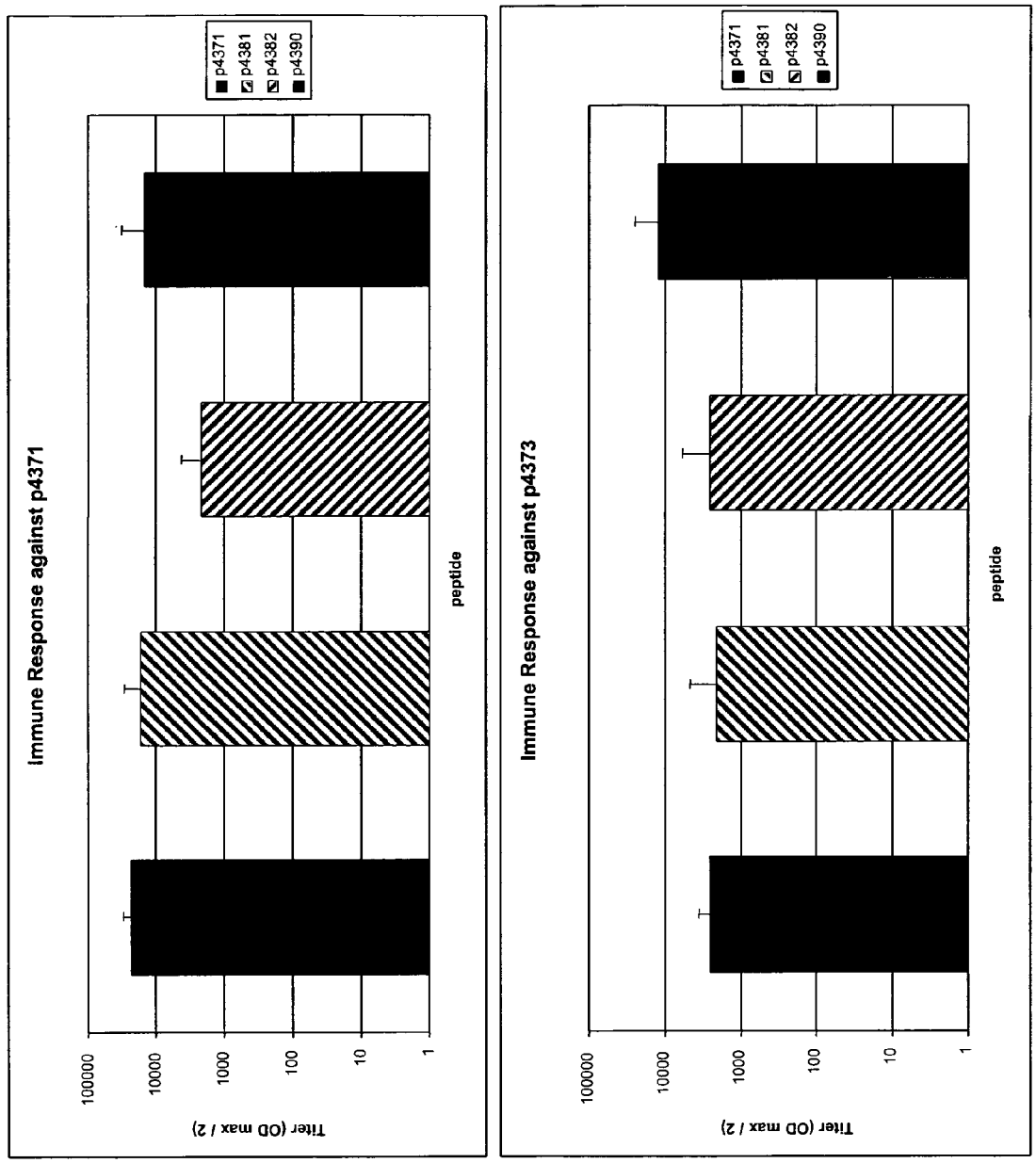

As example for MV-001-mimotopes, original epitope p4371 and the mimotopes p4381, p4382, and p4390 are depicted in FIG. 7C. All Mimotope vaccines depicted mount detectable immune responses against the original epitope p4371. A similar phenomenon as described for MV-003 derived mimotopes can be detected analysing cross reactivity against the pyroglutamate-modified form as displayed by p4373. The original epitope p4371-vaccine and all Mimotope vaccines mount relevant titers against p4373. Surprisingly, the mimotopes selected by MV-001, which is specifically binding to p4371 are inducing a immune reaction cross reacting better with the modified form of the original epitope than the original epitope induced immune reaction or the parental antibody. Thus these mimotopes might surprisingly be able to induce but are not necessarily inducing a broader immune reaction than the parental antibody and can be used for a more wide targeting of forms of Aβ.

Figure 8A:
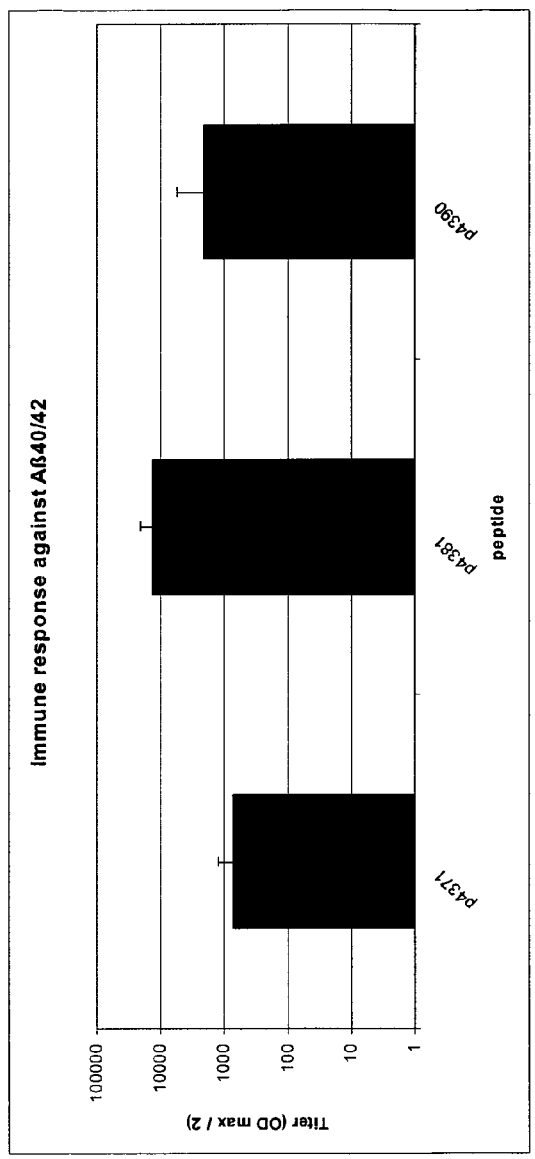
FIG. 8 shows examples for in vivo characterisation of the immune response elicited by mimotope vaccination against full length Aβ40/42.
Figure 8B:
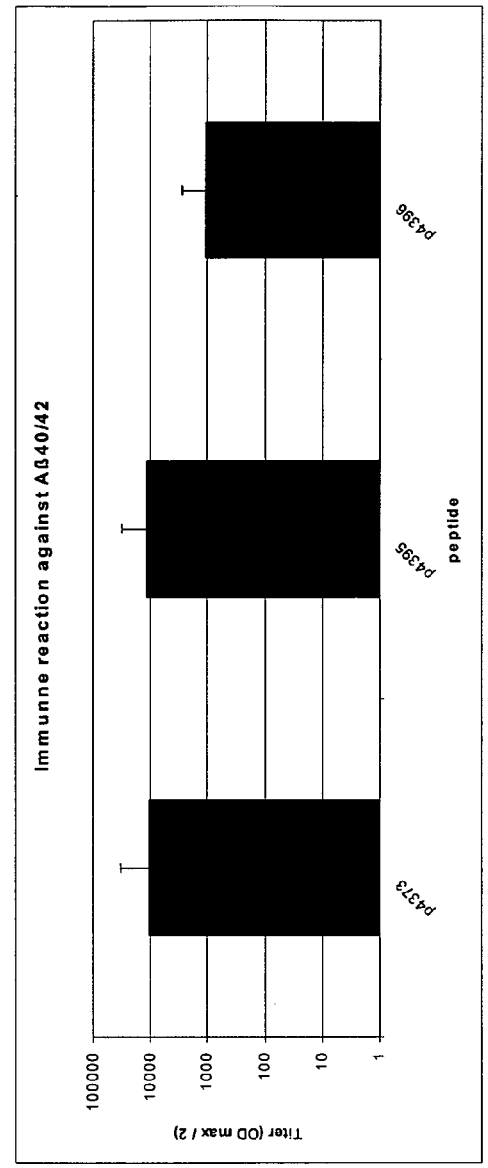

FIG. 8 shows examples for in vivo characterisations of the immune response elicited by mimotope vaccination against full length Aβ. Surprisingly, the mimotopes selected by using MV-001 and MV-003 induce a cross reaction not only with the truncated or modified short epitopes used to create the antibodies but also induce cross reactivity to full length, non modified forms of Aβ as good as the original sequence or even more efficiently than p4371/p4373. For MV-002 original epitope as well as for the mimotopes identified, no such cross reactivity can be detected demonstrating a transfer of specificity of the antibody to the free N-Terminus of unmodified Aβ11-40/42. Thus the mimotopes presented in this invention constitute optimised vaccine candidates to target a broad spectrum of naturally occurring forms of the Aβ peptides as have been found in the brain of AD patients. The forms include but are not limited to Aβ1-40/42, and N-terminally truncated forms like Aβ3-40/42, Aβ(pE)3-40/42 and unmodified Aβ11-40/42 respectively.

In Table 4 and 5 further examples of the immune response elicited by mimotope vaccination against full length Aβ by using MV-001 and MV-003 derived mimotopes are described.

TABLE 4

In vivo characterisation of mimotopes: MV-001

| Internal Peptide number | SEQ ID No. | Detection of Aβ/truncated/modified forms |
|---|---|---|
| p4381 | 19 | + |
| p4383 | 21 | + |
| p4385 | 23 | + |
| p4386 | 24 | + |
| p4390 | 28 | + |
| p4707 | 38 | + |
| p4714 | 45 | + |
| p4715 | 46 | + |
| p4725 | 55 | + |
| p4730 | 59 | + |
| p4738 | 67 | + |
| p4740 | 69 | + |
| p4748 | 77 | + |
| p4753 | 82 | + |

All peptides listed in Table 4 mount specific immune reactions against full length and/or truncated and modified forms of Aβ or fragments thereof.

TABLE 5

In vivo characterisation of mimotopes: MV-003

| Internal Peptide number | SEQ ID No. | Detection of Aβ/truncated/modified forms |
|---|---|---|
| p4395 | 1 | + |
| p4396 | 2 | + |
| p4397 | 3 | + |
| p4399 | 4 | + |

All peptides listed in Table 5 mount specific immune reactions against full length and/or truncated and modified forms of Aβ or fragments thereof.

2.5: In Vivo Characterisation of Mimotopes for the Efficacy to Reduce AD Like Disease in Transgenic Animals The Tg2576 AD mouse model was used to study the preclinical efficacy of the mimotope vaccines. This transgenic line is expressing human APP carrying the Swedish double mutation at aa position 670/671 under the control of a hamster prion protein (PrP) promoter which results in overexpression of the protein. It is currently one of the most widely employed models in AD research. The Tg2576 model recapitulates various hallmarks of AD pathology including disease-specific amyloid plaque deposition and astrocytosis. As all other AD model systems available to date, it does not reflect all cardinal neuropathological features of AD.

To assess whether treatment with mimotopes is capable of preventing cerebral Aβ accumulation, Tg2576 mice were s.c.

injected 6 times at monthly intervals with peptide-KLH conjugates adsorbed to ALUM (adjuvant: aluminium hydroxide) or PBS adsorbed to ALUM (referred to as PBS or control) alone. Up to eight weeks after the last immunization, animals were sacrificed, their brains harvested and analyzed for their Aβ load (AD-like pathology). The mice were sacrificed under deep anaesthesia. Subsequently, the brain was isolated, fixed in 4% PFA and dehydrated by graded Ethanol series followed by incubation in Xylene and paraffin embedding. Each paraffin-embedded brain was sectioned at 7 μM using a slicing microtome and sections were mounted on glass slides.

As a method to assay AD-like pathology in Tg2576 animals, we analyzed the relative area occupied by amyloid deposits in the brain of treated animals. This analysis was performed using an automated area recognition programme. To identify the plaques, sections were stained with the monoclonal antibody (mAb) 3A5 (specific for Aβ40/42). Mimotope treated animals were compared to control animals. All animals have been sacrificed at an age of 13, 5-14 months. For this analysis 3 slides/animal covering the cortex and hippocampus were selected, stained with mAb 3A5 and subsequently documented using the Mirax-system (Zeiss). For the calculation of the area occupied by amyloid plaques, we analysed up to four individual sections per slide and sections carrying tissue artefacts and aberrant staining intensities have been excluded after inspection of the result pictures.

For the mimotopes derived from MV001 an area analysis using three exemplary candidates was performed: Analysis was performed following repeated vaccination using peptide-KLH conjugate vaccines. The control group showed an average occupation of 0.35% as compared to 0.11%, 0.14% and 0.22% for the mimotope treated animals respectively. This corresponds to a reduction following mimotope treatment of 67% in group 2, a 60% reduction in group 3 and a 36% reduction in group 4 (see FIG. 9).

A similar picture can be detected for the group of MV003 derived mimotopes. Here the example of p4395 is depicted. As described for the MV001 derived mimotopes, an analysis of the area occupied by amyloid plaques following peptide-conjugate vaccination has been performed. The control group showed an average occupation of 0.35% as compared to 0.21% for the mimotope treated animals respectively. This corresponds to a reduction following mimotope treatment of 38% in group 2 (see FIG. 10).

Thus, this set of data clearly indicates a beneficial effect of mimotope vaccine treatment on AD like pathology in transgenic animals.

The invention claimed is:

1. An isolated peptide consisting of 7 to 20 amino acid residues, wherein the isolated peptide comprises an amino acid sequence selected from the group consisting of IRWDTP(C) (SEQ ID NO: 106), VRWDVYP(C) (SEQ ID NO: 107), IRYDAPL(C) (SEQ ID NO: 108), IRYDMAG(C) (SEQ ID NO: 109), IRWDTSL(C) (SEQ ID NO: 110), IRWDQP(C) (SEQ ID NO: 111), IRWDG(C) (SEQ ID NO: 112), IRWDGG(C) (SEQ ID NO: 113), EVWHRHQ(C) (SEQ ID NO: 114), ERWHEKH(C) (SEQ ID NO: 115), EVWHRLQ(C) (SEQ ID NO: 116), ELWHRYP(C) (SEQ ID NO: 117), ELWHRAF(C) (SEQ ID NO: 118), ELWHRA(C) (SEQ ID NO: 119), EVWHRG(C) (SEQ ID NO: 120), EVWHRH(C) (SEQ ID NO: 121), ERWHEK(C) (SEQ ID NO: 122), QDFRHY(C) (SEQ ID NO: 123), SEFKHG(C) (SEQ ID NO: 124), TSFRHG(C) (SEQ ID NC): 125), TSVFRH(C) (SEQ ID NO: 126), TPFRHT(C) (SEQ ID NO: 127), SQFRHY(C) (SEQ ID NO: 128), LMFRHN(C) (SEQ ID NO: 129), SAFRHH(C) (SEQ ID NO: 130), LPFRHG(C) (SEQ ID NO: 131), SHFRHG(C) (SEQ ID NO: 132), ILFRHG(C) (SEQ ID NC): 133), QFKHDL(C) (SEQ ID NO: 134), NWFPHP(C) (SEQ ID NO: 135), EEFKYS(C) (SEQ ID NO: 136), NELRHST(C) (SEQ ID NO: 137), GEMRHQP(C) (SEQ ID NO: 138), DTYFPRS(C) (SEQ ID NO: 139), VELRHSR(C) (SEQ ID NO: 140), YSMRHDA(C) (SEQ ID NO: 141), AANYFPR(C) (SEQ ID NO: 142), SPNQFRH(C) (SEQ ID NO: 143), SSSFFPR(C) (SEQ ID NO: 144), EDWFFWH(C) (SEQ ID NO: 145), SAGSFRH(C) (SEQ ID NO: 146), QVMRHHA(C) (SEQ ID NO: 147), SEFSHSS(C) (SEQ ID NO: 148), QPNLFYH(C) (SEQ ID NO: 149), ELFKHHL(C) (SEQ ID NO: 150), TLHEFRH(C) (SEQ ID NO: 151), ATFRHSP(C) (SEQ ID NO: 152), APMYFPH(C) (SEQ ID NO: 153), TYFSHSL(C) (SEQ ID NO: 154), HEPLFSH(C) (SEQ ID NO: 155), SLMRHSS(C) (SEQ ID NO: 156), EFLRHTL(C) (SEQ ID NO: 157), ATPLFRH(C) (SEQ ID NO: 158), QELKRYY(C) (SEQ ID NO: 159), THTDFRH(C) (SEQ ID NO: 160), LHIPFRH(C) (SEQ ID NO: 161), NELFKHF(C) (SEQ ID NO: 162), SQYFPRP(C) (SEQ ID NO: 163), DEHPFRH(C) (SEQ ID NO: 164), MLPFRHG(C) (SEQ ID NO: 165), SAMRHSL(C) (SEQ ID NO: 166), TPLMFWH(C) (SEQ ID NO: 167), LQFKHST(C) (SEQ ID NO: 168), ATFRHST(C) (SEQ ID NO: 169), TGLMFKH(C) (SEQ ID NO: 170), AEFSHWH(C) (SEQ ID NO: 171), QSEFKHW(C) (SEQ ID NO: 172), AEFMHSV(C) (SEQ ID NO: 173), ADHDFRH(C) (SEQ ID NO: 174), DGLLFKH(C) (SEQ ID NO: 175), IGFRHDS(C) (SEQ ID NO: 176), SNSEFRR(C) (SEQ ID NO: 177), SELRHST(C) (SEQ ID NO: 178), THMEFRR(C) (SEQ ID NO: 179), EELRHSV(C) (SEQ ID NO: 180), QLFKHSP(C) (SEQ ID NO: 181), YEFRHAQ(C) (SEQ ID NO: 182), SNFRHSV(C) (SEQ ID NO: 183), APIQFRH(C) (SEQ ID NO: 184), AYFPHTS(C) (SEQ ID NO: 185), NSSELRH(C) (SEQ ID NO: 186), TEFRHKA(C) (SEQ ID NO: 187), TSTEMWH(C) (SEQ ID NO: 188), SQSYFKH(C) (SEQ ID NO: 189), (C)SEFKH (SEQ ID NO: 190), SEFKH(C) (SEQ ID NO: 191), (C)HEFRH (SEQ ID NO: 192) and HEFRH(C) (SEQ ID NO: 193).

2. A compound comprising the peptide of claim 1 coupled to a pharmaceutically acceptable carrier.

3. A pharmaceutical formulation comprising the peptide of claim 1.

4. A vaccine comprising the peptide of claim 1.

5. A process for treating β-amyloidoses, the process comprising administering to an individual a medicament comprising a compound comprising an amino acid sequence selected from the group consisting of EVWHRHQ(C) (SEQ ID NO: 114), ERWHEKH(C) (SEQ ID NO: 115), EVWHRLQ(C) (SEQ ID NO: 116), ELWHRYP(C) (SEQ ID NO: 117), ELWHRAF(C) (SEQ ID NO: 118), ELWHRA(C) (SEQ ID NO: 119), EVWHRG(C) (SEQ ID NO: 120), EVWHRH(C) (SEQ ID NO: 121), ERWHEK(C) (SEQ ID NO: 122), QDFRHY(C) (SEQ ID NO: 123), SEFKHG(C) (SEQ ID NO: 124), TSFRHG(C) (SEQ ID NO: 125), TSVFRH(C) (SEQ ID NO: 126), TPFRHT(C) (SEQ ID NO: 127), SQFRHY(C) (SEQ ID NO: 128), LMFRHN(C) (SEQ ID NO: 129), SAFRHH(C) (SEQ ID NO: 130), LPFRHG(C) (SEQ ID NO: 131), SHFRHG(C) (SEQ ID NO: 132), ILFRHG(C) (SEQ ID NO: 133), QFKHDL(C) (SEQ ID NO: 134), NWFPHP(C) (SEQ ID NO: 135), EEFKYS(C) (SEQ ID NO: 136), NELRHST(C) (SEQ ID NO: 137), GEMRHQP(C) (SEQ ID NO: 138), DTYFPRS(C) (SEQ ID NO: 139), VELRHSR(C) (SEQ ID NO: 140), YSMRHDA(C) (SEQ ID NO: 141), AANYFPR(C) (SEQ ID NO: 142), SPNQFRH(C) (SEQ ID NO: 143), SSSFFPR(C) (SEQ ID NO: 144), EDWFFWH(C) (SEQ ID NO: 145), SAGSFRH(C) (SEQ ID NO: 146), QVMRHHA(C) (SEQ ID NO: 147), SEFSHSS(C) (SEQ ID NO: 148), QPNLFYH(C) (SEQ ID NO: 149), ELFKHHL(C) (SEQ ID NO: 150), TLHEFRH(C) (SEQ ID NO: 151), ATFRHSP(C) (SEQ ID NO: 152), APMYFPH(C) (SEQ ID NO: 153), TYFSHSL(C) (SEQ ID NO: 154), HEPLFSH(C) (SEQ ID NO: 155), SLMRHSS(C) (SEQ ID NO: 156), EFLRHTL(C) (SEQ ID NO: 157), ATPLFRH(C) (SEQ ED NO: 158), QELKRYY(C) (SEQ ID NO: 159), THTDFRH(C) (SEQ ID NO: 160), LHIPFRH(C) (SEQ ID NO: 161), NELFKHF(C) (SEQ ID NO: 162), SQYFPRP(C) (SEQ ID NO: 163), DEHPFRH(C) (SEQ ID NO: 164), MLPFRHG(C) (SEQ ID NO: 165), SAMRHSL(C) (SEQ ID NO: 166), TPLMFWH(C) (SEQ ID NO: 167), LQFKHST(C) (SEQ ID NO: 168), ATFRHST(C) (SEQ ID NO: 169), TGLMFKH(C) (SEQ ID NO: 170), AEFSHWH(C) (SEQ ID NO: 171), QSEFKHW(C) (SEQ ID NO: 172), AEFMHSV(C) (SEQ ID NO: 173), ADHDFRH(C) (SEQ ID NO: 174), DGLLFKH(C) (SEQ ID NO: 175), IGFRHDS(C) (SEQ ID NO: 176), SNSEFRR(C) (SEQ ID NO: 177), SELRHST(C) (SEQ ID NO: 178), THMEFRR(C) (SEQ ID NO: 179), EELRHSV(C) (SEQ ID NO: 180), QLFKHSP(C) (SEQ ID NO: 181), YEFRHAQ(C) (SEQ ID NO: 182), SNFRHSV(C) (SEQ ED NO: 183), APIQFRH(C) (SEQ ID NO: 184), AYFPHTS(C) (SEQ ID NO: 185), NSSELRH(C) (SEQ ID NO: 186), TEFRHKA(C) (SEQ ID NO: 187), TSTEMWH(C) (SEQ ID NO: 188), SQSYFKH(C) (SEQ ID NO: 189), (C)SEFKH (SEQ ID NO: 190), SEFKH(C) (SEQ ID NO: 191), (C)HEFRH (SEQ ID NO: 192) and HEFRH(C) (SEQ ID NO: 193).

6. The process of claim 5, wherein the compound comprises an amino acid sequence selected from the group consisting of QDFRHY(C) (SEQ ID NO: 123), SEFKHG(C) (SEQ ID NO: 124), TSFRHG(C) (SEQ ID NO: 125), TSVFRH(C) (SEQ ID NO: 126), TPFRHT(C) (SEQ ID NO: 127), SQFRHY(C) (SEQ ID NO: 128), LMFRHN(C) (SEQ ID NO: 129), SAFRHH(C) (SEQ ID NO: 130), LPFRHG(C) (SEQ ID NO: 131), SHFRHG(C) (SEQ ID NO: 132), ILFRHG(C) (SEQ ID NO: 133), QFKHDL(C) (SEQ ID NO: 134), NWFPHP(C) (SEQ ID NO: 135), EEFKYS(C) (SEQ ID NO: 136), SPNQFRH(C) (SEQ ID NO: 143), ELFKHHL(C) (SEQ ID NO: 150), TLHEFRH(C) (SEQ ID NO: 151), THTDFRH(C) (SEQ ID NO: 160), DEHPFRH(C) (SEQ ID NO: 164), QSEFKHW(C) (SEQ ID NO: 172), ADHDFRH(C) (SEQ ID NO: 174), DGLLFKH(C) (SEQ ID NO: 175), EELRHSV(C) (SEQ ID NO: 180), YEFRHAQ(C) (SEQ ID NO: 182), TEFRHKA(C) (SEQ ID NO: 187), (C)SEFKH (SEQ ID NO: 190), SEFKH(C) (SEQ ID NO: 191), (C)HEFRH (SEQ ID NO: 192) and HEFRH(C) (SEQ ID NO: 193).

7. The process of claim 5, wherein the compound is a polypeptide consisting of 7 to 20 amino acid residues.

8. The process of claim 5, wherein the compound is coupled to a pharmaceutically acceptable carrier.

9. The process of claim 8, wherein the pharmaceutically acceptable carrier is KLH (Keyhole Limpet Hemocyanin).

10. The process of claim 5, wherein the compound is formulated for intravenous, subcutaneous, intradermal or intramuscular administration.

11. The process of claim 5, wherein the compound is formulated with an adjuvant.

12. The process of claim 11, wherein the adjuvant is aluminium hydroxide.

13. The process of claim 5, wherein the medicament comprises 0.1 ng to 10 mg of the compound.

14. The process of claim 5, wherein the compound comprises an amino acid sequence selected from the group consisting of SEFKHG(C) (SEQ ID NO: 124), TLHEFRH(C) (SEQ ID NO: 151), ILFRHG(C) (SEQ ID NO: 133), TSVFRH(C) (SEQ ID NO: 126), SQFRHY(C) (SEQ ID NO: 128), LMFRHN(C) (SEQ ID NO: 129), SPNQFRH(C) (SEQ ID NO: 143), ELFKHHL(C) (SEQ ID NO: 150), THTDFRH(C) (SEQ ID NO: 160), DEHPFRH(C) (SEQ ID NO: 164), QSEFKHW(C) (SEQ ID NO: 172), ADHDFRH(C) (SEQ ID NO: 174), YEFRHAQ(C) (SEQ ID NO: 182) and TEFRHKA(C) (SEQ ID NO: 187).

15. The process of claim 5, wherein the compound comprises an amino acid sequence selected from the group consisting of EVWHRHQ(C) (SEQ ID NO: 114), ERWHEKH(C) (SEQ ID NO: 115), EVWHRLQ(C) (SEQ ID NO: 116), ELWHRYP(C) (SEQ ID NO: 117), ELWHRAF(C) (SEQ ID NO: 118), ELWHRA(C) (SEQ ID NO: 119), EVWHRG(C) (SEQ ID NO: 120), EVWHRH(C) (SEQ ID NO: 121) and ERWHEK(C) (SEQ ID NO: 122).

* * * * *